US012053308B2

(12) United States Patent
Alcaide et al.

(10) Patent No.: US 12,053,308 B2
(45) Date of Patent: Aug. 6, 2024

(54) BRAIN-COMPUTER INTERFACE WITH ADAPTATIONS FOR HIGH-SPEED, ACCURATE, AND INTUITIVE USER INTERACTIONS

(71) Applicant: Neurable Inc., Boston, MA (US)

(72) Inventors: Ramses Alcaide, Boston, MA (US); Dereck Padden, Newton, MA (US); Jay Jantz, Burlington, MA (US); James Hamet, Cambridge, MA (US); Jeffrey Morris, Jr., Cambridge, MA (US); Arnaldo Pereira, Acton, MA (US)

(73) Assignee: Neurable Inc., Boston, MA (US)

( * ) Notice: Subject to any disclaimer, the term of this patent is extended or adjusted under 35 U.S.C. 154(b) by 996 days.

(21) Appl. No.: 16/926,331

(22) Filed: Jul. 10, 2020

(65) Prior Publication Data

US 2020/0337653 A1    Oct. 29, 2020

Related U.S. Application Data

(63) Continuation of application No. PCT/US2019/014315, filed on Jan. 18, 2019.
(Continued)

(51) Int. Cl.
*A61B 5/00* (2006.01)
*A61B 5/16* (2006.01)
(Continued)

(52) U.S. Cl.
CPC ............ *A61B 5/7435* (2013.01); *A61B 5/163* (2017.08); *A61B 5/378* (2021.01); *A61B 5/7264* (2013.01);
(Continued)

(58) Field of Classification Search
None
See application file for complete search history.

(56) References Cited

U.S. PATENT DOCUMENTS 4,013,068 A    3/1977    Settle et al.
4,158,196 A    6/1979    Crawford, Jr.
(Continued)

FOREIGN PATENT DOCUMENTS

CA    2765500 A1    12/2010
CN    1927551 A    3/2007
(Continued)

OTHER PUBLICATIONS

Amyotrophic Lateral Sclerosis (ALS) Fact Sheet, National Institute of Neurological Disorders and Stroke (Jun. 2013), 12 pages.
(Continued)

*Primary Examiner* — Amare Mengistu
*Assistant Examiner* — Sarvesh J Nadkarni
(74) *Attorney, Agent, or Firm* — Cooley LLP

(57) ABSTRACT

Embodiments described herein relate to systems, devices, and methods for use in the implementation of a brain-computer interface that tracks brain activity, with or without additional sensors providing additional sources of information, while presenting and updating a User Interface/User Experience that is strategically designed for high speed and accuracy of human-machine interaction. Embodiments described herein also relate to the implementation of a hardware agnostic brain-computer interface that uses neural signals to mediate user manipulation of machines and devices.

20 Claims, 21 Drawing Sheets

Related U.S. Application Data

(60) Provisional application No. 62/618,846, filed on Jan. 18, 2018.

(51) Int. Cl.

| | | |
|---|---|---|
| *A61B 5/378* | (2021.01) | |
| *G06F 3/01* | (2006.01) | |
| *G06F 3/023* | (2006.01) | |
| *G06F 3/04842* | (2022.01) | |

(52) U.S. Cl.
CPC .......... *A61B 5/7475* (2013.01); *G06F 3/013* (2013.01); *G06F 3/015* (2013.01); *G06F 3/0236* (2013.01); *G06F 3/04842* (2013.01)

(56) References Cited

U.S. PATENT DOCUMENTS

| | | | |
|---|---|---|---|
| 4,595,990 A | 6/1986 | Garwin et al. | |
| 5,137,027 A | 8/1992 | Rosenfeld | |
| 5,213,338 A | 5/1993 | Brotz | |
| 5,269,325 A | 12/1993 | Robinson et al. | |
| 5,325,862 A | 7/1994 | Lewis et al. | |
| 5,339,826 A | 8/1994 | Schmidt et al. | |
| 5,342,410 A | 8/1994 | Braverman | |
| 5,467,777 A | 11/1995 | Farwell | |
| 5,638,826 A | 6/1997 | Wolpaw et al. | |
| 5,692,517 A | 12/1997 | Junker | |
| 5,742,286 A | 4/1998 | Kung et al. | |
| 5,899,867 A | 5/1999 | Collura | |
| 5,931,908 A | 8/1999 | Gerba et al. | |
| 5,967,996 A | 10/1999 | Kadota et al. | |
| 5,983,129 A | 11/1999 | Cowan et al. | |
| 6,090,051 A | 7/2000 | Marshall | |
| 6,323,884 B1 | 11/2001 | Bird et al. | |
| 6,380,937 B1 | 4/2002 | Dong et al. | |
| 6,712,468 B1 | 3/2004 | Edwards | |
| 6,847,844 B2 | 1/2005 | Sun et al. | |
| 6,917,370 B2 | 7/2005 | Benton | |
| 7,084,884 B1 | 8/2006 | Nelson et al. | |
| 7,120,486 B2 | 10/2006 | Leuthardt et al. | |
| 7,546,158 B2 | 6/2009 | Allison et al. | |
| 7,580,742 B2 | 8/2009 | Tan et al. | |
| 7,835,787 B2 | 11/2010 | Sajda et al. | |
| 8,155,736 B2 | 4/2012 | Sullivan et al. | |
| 8,244,475 B2 | 8/2012 | Aguilar et al. | |
| 8,594,814 B2 | 11/2013 | Rovaglio et al. | |
| 8,878,785 B1 | 11/2014 | Nordstrom | |
| 9,183,560 B2 | 11/2015 | Abelow | |
| 9,210,517 B2 | 12/2015 | Pontoppidan et al. | |
| 9,389,685 B1 | 7/2016 | Pathirage et al. | |
| 9,468,541 B2 | 10/2016 | Contreras-Vidal et al. | |
| 9,532,748 B2 | 1/2017 | Denison et al. | |
| 9,563,273 B2 | 2/2017 | Mann | |
| 9,629,976 B1 | 4/2017 | Acton | |
| 9,743,002 B2 | 8/2017 | Wierich | |
| 10,664,050 B2 | 5/2020 | Alcaide et al. | |
| 11,266,342 B2 | 3/2022 | Huggins et al. | |
| 11,269,414 B2 | 3/2022 | Alcaide et al. | |
| 11,366,517 B2 | 6/2022 | Alcaide et al. | |
| 2002/0036381 A1 | 3/2002 | Scibetta | |
| 2002/0065851 A1 | 5/2002 | Watson et al. | |
| 2003/0031457 A1 | 2/2003 | Miomo et al. | |
| 2003/0195798 A1 | 10/2003 | Goci | |
| 2003/0203342 A1 | 10/2003 | Bowers | |
| 2004/0043372 A1 | 3/2004 | Jebb et al. | |
| 2004/0092809 A1 | 5/2004 | DeCharms | |
| 2004/0169673 A1 | 9/2004 | Crampe et al. | |
| 2004/0249302 A1 | 12/2004 | Donoghue et al. | |
| 2005/0017870 A1 | 1/2005 | Allison et al. | |
| 2005/0046698 A1 | 3/2005 | Knight | |
| 2005/0085744 A1 | 4/2005 | Beverina et al. | |
| 2005/0131311 A1 | 6/2005 | Leuthardt et al. | |
| 2005/0170325 A1 | 8/2005 | Steinberg et al. | |
| 2005/0191609 A1 | 9/2005 | Fadel et al. | |
| 2005/0222873 A1 | 10/2005 | Nephin et al. | |
| 2005/0226505 A1 | 10/2005 | Wilson | |
| 2006/0093998 A1* | 5/2006 | Vertegaal | G06F 3/011 |
| | | | 705/7.29 |
| 2007/0066914 A1 | 3/2007 | Le et al. | |
| 2007/0086773 A1 | 4/2007 | Ramsten et al. | |
| 2007/0166675 A1 | 7/2007 | Atkins et al. | |
| 2007/0166686 A1 | 7/2007 | Foster | |
| 2007/0173733 A1 | 7/2007 | Le et al. | |
| 2007/0179396 A1 | 8/2007 | Le et al. | |
| 2008/0024724 A1 | 1/2008 | Todd | |
| 2008/0065468 A1 | 3/2008 | Berg et al. | |
| 2008/0218472 A1 | 9/2008 | Breen et al. | |
| 2008/0228242 A1 | 9/2008 | Fink et al. | |
| 2008/0317206 A1 | 12/2008 | Yoshino | |
| 2009/0082692 A1 | 3/2009 | Hale et al. | |
| 2009/0086165 A1 | 4/2009 | Beymer | |
| 2009/0099623 A1 | 4/2009 | Bentwich | |
| 2009/0125849 A1 | 5/2009 | Bouvin et al. | |
| 2009/0175540 A1 | 7/2009 | Dariush et al. | |
| 2009/0289895 A1 | 11/2009 | Nakada et al. | |
| 2009/0319058 A1 | 12/2009 | Rovaglio et al. | |
| 2010/0010391 A1 | 1/2010 | Skelton et al. | |
| 2010/0039438 A1 | 2/2010 | Kennedy | |
| 2010/0100001 A1 | 4/2010 | Aguilar et al. | |
| 2010/0145215 A1* | 6/2010 | Pradeep | A61B 5/377 |
| | | | 600/546 |
| 2010/0191140 A1 | 7/2010 | Terada et al. | |
| 2010/0223549 A1 | 9/2010 | Edwards | |
| 2010/0240016 A1 | 9/2010 | Ween et al. | |
| 2010/0280403 A1 | 11/2010 | Erdogmus et al. | |
| 2010/0317988 A1 | 12/2010 | Terada et al. | |
| 2011/0004089 A1 | 1/2011 | Chou | |
| 2011/0148927 A1 | 6/2011 | Tainsh et al. | |
| 2011/0152710 A1 | 6/2011 | Kim et al. | |
| 2011/0159467 A1 | 6/2011 | Peot et al. | |
| 2011/0175932 A1 | 7/2011 | Yu et al. | |
| 2011/0301486 A1 | 12/2011 | Van Hek et al. | |
| 2012/0019662 A1 | 1/2012 | Maltz | |
| 2012/0034583 A1 | 2/2012 | Dujowich et al. | |
| 2012/0036097 A1 | 2/2012 | Prokhorov | |
| 2012/0044154 A1 | 2/2012 | Black et al. | |
| 2012/0150545 A1 | 6/2012 | Simon | |
| 2012/0254745 A1 | 10/2012 | Sangiovanni et al. | |
| 2012/0287284 A1 | 11/2012 | Jacobsen et al. | |
| 2012/0289854 A1 | 11/2012 | Yamada et al. | |
| 2012/0296476 A1 | 11/2012 | Cale et al. | |
| 2013/0050432 A1 | 2/2013 | Perez et al. | |
| 2013/0125027 A1 | 5/2013 | Abovitz | |
| 2013/0130799 A1 | 5/2013 | Van Hulle et al. | |
| 2013/0169560 A1 | 7/2013 | Cederlund et al. | |
| 2013/0335573 A1 | 12/2013 | Forutanpour et al. | |
| 2014/0058528 A1 | 2/2014 | Contreras-Vidal et al. | |
| 2014/0065594 A1 | 3/2014 | Venable | |
| 2014/0096077 A1 | 4/2014 | Jacob et al. | |
| 2014/0223462 A1 | 8/2014 | Aimone et al. | |
| 2014/0225918 A1 | 8/2014 | Mittal et al. | |
| 2014/0228701 A1 | 8/2014 | Chizeck et al. | |
| 2014/0247232 A1 | 9/2014 | George-Svahn et al. | |
| 2014/0316230 A1 | 10/2014 | Denison et al. | |
| 2014/0320397 A1 | 10/2014 | Hennessey et al. | |
| 2014/0320817 A1 | 10/2014 | Kiderman et al. | |
| 2014/0347265 A1 | 11/2014 | Aimone et al. | |
| 2014/0372957 A1 | 12/2014 | Keane et al. | |
| 2015/0042558 A1 | 2/2015 | Massonneau et al. | |
| 2015/0199010 A1 | 7/2015 | Coleman et al. | |
| 2015/0212576 A1 | 7/2015 | Ambrus et al. | |
| 2015/0212695 A1 | 7/2015 | Nordstrom et al. | |
| 2015/0338915 A1* | 11/2015 | Publicover | G06F 3/0304 |
| | | | 345/633 |
| 2016/0077547 A1 | 3/2016 | Aimone et al. | |
| 2016/0103484 A1 | 4/2016 | Guo et al. | |
| 2016/0187976 A1 | 6/2016 | Levesque et al. | |
| 2016/0198091 A1 | 7/2016 | Edwards | |
| 2016/0235323 A1 | 8/2016 | Tadi et al. | |
| 2016/0253890 A1 | 9/2016 | Rabinowitz et al. | |
| 2016/0259519 A1 | 9/2016 | Foss et al. | |
| 2016/0259528 A1 | 9/2016 | Foss et al. | |
| 2017/0078447 A1 | 3/2017 | Hancock et al. | |

(56) References Cited

U.S. PATENT DOCUMENTS

| | | |
|---|---|---|
| 2017/0124928 A1 | 5/2017 | Edwin et al. |
| 2017/0139556 A1 | 5/2017 | Josephson |
| 2017/0188933 A1 | 7/2017 | Huggins et al. |
| 2017/0249009 A1 | 8/2017 | Parshionikar |
| 2017/0290504 A1 | 10/2017 | Khaderi et al. |
| 2017/0293356 A1 | 10/2017 | Khaderi et al. |
| 2017/0316707 A1 | 11/2017 | Lawrenson et al. |
| 2017/0322679 A1 | 11/2017 | Gordon |
| 2017/0323615 A1 | 11/2017 | Hazra et al. |
| 2018/0008141 A1 | 1/2018 | Krueger |
| 2018/0039329 A1* | 2/2018 | Tumey .................. G06F 3/011 |
| 2018/0321739 A1 | 11/2018 | Park |
| 2018/0364810 A1 | 12/2018 | Parshionikar |
| 2019/0246982 A1 | 8/2019 | Mackellar et al. |
| 2019/0286234 A1 | 9/2019 | Condolo |
| 2020/0268296 A1 | 8/2020 | Alcaide et al. |
| 2021/0113129 A1 | 4/2021 | Huang |
| 2021/0141453 A1 | 5/2021 | Miller, III |
| 2022/0404910 A1 | 12/2022 | Alcaide et al. |
| 2023/0107040 A1 | 4/2023 | Alcaide et al. |

FOREIGN PATENT DOCUMENTS

| | | |
|---|---|---|
| CN | 101339455 A | 1/2009 |
| CN | 101515199 A | 8/2009 |
| CN | 101515199 B | 1/2011 |
| CN | 102098639 A | 6/2011 |
| CN | 103092340 A | 5/2013 |
| CN | 103421859 A | 12/2013 |
| CN | 103793058 A | 5/2014 |
| CN | 103955269 A | 7/2014 |
| CN | 104837088 A | 8/2015 |
| CN | 105051647 A | 11/2015 |
| CN | 107072583 A | 8/2017 |
| EP | 2613222 A1 | 7/2013 |
| JP | H10260773 A | 9/1998 |
| JP | H1165794 A | 3/1999 |
| JP | 2002236957 A | 8/2002 |
| JP | 2003058298 A | 2/2003 |
| JP | 2010015584 A | 1/2010 |
| JP | 4465414 B2 | 5/2010 |
| JP | 2010218491 A | 9/2010 |
| JP | 2012053656 A | 3/2012 |
| JP | 2012221498 A | 11/2012 |
| JP | 2013004006 A | 1/2013 |
| JP | 2013190942 A | 9/2013 |
| JP | 2013244116 A | 12/2013 |
| JP | 2016126773 A | 7/2016 |
| JP | 2016207115 A | 12/2016 |
| JP | 2017058971 A | 3/2017 |
| JP | 2018505457 A | 2/2018 |
| JP | 2018529171 A | 10/2018 |
| JP | 2020503906 A | 2/2020 |
| KR | 101023249 B1 | 3/2011 |
| KR | 20150081846 A | 7/2015 |
| KR | 101579364 B1 | 12/2015 |
| KR | 20150140286 A | 12/2015 |
| KR | 20160061699 A | 6/2016 |
| KR | 101723841 B1 | 4/2017 |
| RU | 2627075 C | 8/2017 |
| WO | WO-02091119 A2 | 11/2002 |
| WO | WO-03037231 A1 | 5/2003 |
| WO | WO-2004073485 A2 | 9/2004 |
| WO | WO-2005079332 A2 | 9/2005 |
| WO | WO-2006051709 A1 | 5/2006 |
| WO | WO-2007044431 A2 | 4/2007 |
| WO | WO-2007086222 A1 | 8/2007 |
| WO | WO-2009056650 A1 | 5/2009 |
| WO | WO-2009089532 A1 | 7/2009 |
| WO | WO-2009093435 A1 | 7/2009 |
| WO | WO-2009139119 A1 | 11/2009 |
| WO | WO-2010147913 A1 | 12/2010 |
| WO | WO-2011105000 A1 | 9/2011 |
| WO | WO-2011140303 A1 | 11/2011 |
| WO | WO-2012020906 A1 | 2/2012 |
| WO | WO-2012071544 A2 | 5/2012 |
| WO | WO-2012137801 A1 | 10/2012 |
| WO | WO-2013012739 A1 | 1/2013 |
| WO | WO-2014116826 A1 | 7/2014 |
| WO | WO-2014144940 A2 | 9/2014 |
| WO | WO-2016064314 A1 | 4/2016 |
| WO | WO-2016073131 A1 | 5/2016 |
| WO | WO-2016193979 A1 | 12/2016 |
| WO | WO-2017031089 A1 | 2/2017 |
| WO | WO-2017046698 A1 | 3/2017 |
| WO | WO-2017104869 A1 | 6/2017 |
| WO | WO-2018064627 A1 | 4/2018 |
| WO | WO-2018127782 A1 | 7/2018 |

OTHER PUBLICATIONS

Aref, A. W., "The P300-Certainty Algorithm: Improving accuracy by withholding erroneous selections," ECNS Conference, Bristol, Tennessee, Sep. 12-16, 2012, p. 79.

Bai, O. et al., "Exploration of computational methods for classification of movement intention during human voluntary movement from single trial EEG," Clin. Neurophysiol., 118:2637-2655 (2007).

Bai, O. et al., "Towards a User-Friendly Brain-Computer Interface: Initial Tests in ALS and PLS Patients," Clin. Neurophysiol., 121:1293-1303 (2010).

Bashashati, A. et al., "A survey of signal processing algorithms in braincomputer interfaces based on electrical brain signals," J. Neural. Eng., 4:R32-R57 (2007).

Cipresso, P. et al., "The combined use of Brain Computer Interface and Eye-Tracking technology for cognitive assessment in Amyotrophic Lateral Sclerosis," 2011 5th International Conference on Pervasive Computing Technologies for Healthcare and Workshops, Pervasive Health 2011, 5 pages.

Cipresso, P. et al., "The use of P300based BCIs in amyotrophic lateral sclerosis: from augmentative and alternative communication to cognitive assessment," Brain and Behavior, 2(4):479-498 (2012).

Communication pursuant to Article 94(3) for European Application No. EP18875541.7 dated Feb. 2, 2024, 5 pages.

Communication pursuant to Article 94(3) dated Jan. 23, 2024 for European Application No. 19861902.5, 5 pages.

Communication pursuant to Article 94(3) dated Jan. 25, 2023 for European Application No. 18848298.8, 9 pages.

Connolly, J. F. & D'Arcy, R. C., "Innovations in neuropsychological assessment using event-related brain potentials," Int. J. Psychophysiol., 37:31-47 (2000).

Connolly, J. F. et al., "Performance on WISC-III and WAIS-R NI vocabulary subtests assessed with event-related brain potentials: an innovative method of assessment," J. Clin. Exp. Neurophsychol., 21:444-464 (2010).

D'arcy, R. C. et al., "Electrophysiological assessment of language function following stroke," Clin. Neurophysiol., 114:662-672 (2003).

D'arcy, R. C. et al., "Evaluation of reading comprehension with neuropsychological and event-related brain potential (ERP) methods," J. Int. Neurophyschol. Soc., 6(5):556-567 (2000).

Examination Report dated Oct. 4, 2023 for European Application No. 19741853.6, 5 pages.

Extended European Search Report dated Apr. 19, 2018 for European Application No. 15799099.5, 13 pages.

Extended European Search Report dated Apr. 19, 2021 for European Application No. 18848298.8, 15 pages.

Extended European Search Report dated Apr. 28, 2022 for European Application No. 19861902.5, 7 pages.

Extended European Search Report dated Jan. 24, 2022 for European Application No. 19741853.6, 12 pages.

Extended European Search Report dated Jul. 14, 2021 for European Application No. 18875541.7, 10 pages.

Final Notice of Reasons for Rejection dated Sep. 20, 2023 for Japanese Application No. 2020-544378, with English translation, 11 pages.

Final Notice of Reasons for Rejection for Japanese Application No. JP20200532856 dated Jan. 23, 2024, with English translation, 5 pages.

(56) References Cited

OTHER PUBLICATIONS

Final Office Action for U.S. Appl. No. 16/872,730, dated Jan. 18, 2023, 33 pages.
Final Office Action mailed Mar. 12, 2021 for U.S. Appl. No. 15/305,030, 13 pages.
Hampshire, A. et al., "Assessing residual reasoning ability in overtly non-communicative patients using fMRI," Neuroimage: Clinical, 2:174-183 (2012).
Heun, V. et al., "Smarter Objects: Using AR technology to Program Physical Objects and their Interactions," CH 2013 Extended Abstracts, Apr. 27-May 2, 2013, pp. 961-966 (2013), XP058015943.
International Search Report and Written Opinion mailed Aug. 31, 2015 for International Application No. PCT/2015/032192, 9 pages.
International Search Report and Written Opinion mailed Dec. 18, 2019 for International Application No. PCT/US19/51997, 20 pages.
International Search Report and Written Opinion mailed Jan. 22, 2019 for International Application No. PCT/US2018/060797, 10 pages.
International Search Report and Written Opinion mailed Jun. 20, 2019 for International Application No. PCT/US19/14315, 16 pages.
International Search Report and Written Opinion mailed Oct. 22, 2018 for International Application No. PCT/US2018/047598, 17 pages.
Iverson, I. H. et al., "A braincomputer interface tool to assess cognitive functions in completely paralyzed patients with amyotrophic lateral sclerosis," Clin. Neurophysiol., 119:2214-2223 (2008).
Jiang, J., et al., "Hybrid Brain-Computer Interface (BCI) based on the EEG and EOG signals, Bio-Medical Materials and Engineering," 2014, vol. 24, No. 6, pp. 2919-2925, [Online; retrieval date: Jan. 24, 2023], Internet, URL: https://content.iospress.com/articles/bio-medical-materialsand-engineering/bme1111, DOI:10.3233/BME-141111.
Kübler, A. et al., "Brain-Computer Interfaces and communication in paralysis: extinction of goal directed thinking in completely paralysed patients?" Clin. Neurophysiol., 119:2658-2666 (2008).
Makeig, S. et al., "Evolving Signal Processing for BrainComputer Interfaces," Proc. of the IEEE, 100:1567-1584 (2012).
Martens, S. M. M. et al., "Overlap and refractory effects in a brain-computer interface speller based on the visual P300 event related potential; Overlap and refractory effects in a BCI speller based on the visual P300 ERP," Journal of Neural Engineering, 6(2):1741-2552 (2009).
Mohsenzadeh, Y. et al., "A State Space Model for Spatial Updating of Remembered Visual Targets during Eye Movements," Frontiers in Systems Neuroscience, vol. 10, May 12, 2016; 10:39, 22 pages; doi:10.3389/fnsys.2016.00039.
Murguialday, R. A. et al., "Brain-Computer Interface for a Prosthetic Hand Using Local Machine Control and Haptic Feedback," 10th International Conference on Rehabilitation Robotics, IEEE, pp. 609-613 (2007).
Naci, L. et al., "BrainComputer Interfaces for Communication with Nonresponsive Patients," Ann. Neurol., 72:312-323 (2012).
Nishino, S., et al., Abstract "A Basic Study on Speeding up Japanese Input BCI with Linguistic Feature, IEICE Technical Report AI2016-1-AI2016-11, Artificial Intelligence and Knowledge-Based Processing", Japan, The Institute of Electronics, Information and Communication Engineers, vol. 116, No. 117, Jun. 20, 2016, 4 pages.
Non-Final Office Action for U.S. Appl. No. 16/872,730 dated Aug. 10, 2023, 39 pages.
Non-Final Office Action for U.S. Appl. No. 17/747,735 dated Jul. 3, 2023, 13 pages.
Non-Final Office Action mailed Aug. 15, 2019 for U.S. Appl. No. 16/138,791, 12 pages.
Non-Final Office Action mailed Aug. 31, 2021 for U.S. Appl. No. 15/305,030, 17 pages.
Non-Final Office Action mailed Jan. 13, 2020 for U.S. Appl. No. 15/305,030, 12 pages.
Non-Final Office Action mailed Jan. 25, 2023 for U.S. Appl. No. 17/589,175, 16 pages.
Non-Final Office Action mailed Jul. 28, 2021 for U.S. Appl. No. 16/847,020, 14 pages.
Non-Final Office Action mailed Jun. 12, 2019 for U.S. Appl. No. 15/305,030, 10 pages.
Non-Final Office Action mailed Jun. 27, 2022 for U.S. Appl. No. 16/872,730, 29 pages.
Non-Final Office Action mailed Nov. 19, 2020 for U.S. Appl. No. 15/305,030, 13 pages.
Non-Final Office Action mailed Apr. 14, 2021 for U.S. Appl. No. 16/797,376, 18 pages.
Notice of Preliminary Rejection for Korean Application No. KR1020207008357 dated Sep. 27, 2023, with English translation, 18 pages.
Notice of Reasons for Rejection dated Apr. 25, 2023 for Japanese Application No. JP20200532856, with English translation, 11 pages.
Notice of Reasons for Rejection for Japanese Application No. JP2020544378 dated Dec. 2, 2022, 10 pages, with English translation, 10 pages.
Notice of Reasons for Rejection mailed Aug. 2, 2022 for Japanese Application No. JP20200532856, with English translation, 9 pages.
Office Action and Search report for Chinese Application No. CN201880069216 dated Dec. 11, 2023, with English translation, 10 pages.
Office Action and Search Report for Chinese Application No. CN201880085323 dated Jan. 16, 2024, with English translation, 10 pages.
Office Action and Search Report for Chinese Application No. CN20188069216 dated Mar. 4, 2023, with English translation, 20 pages.
Office Action and Search report for Chinese Application No. CN20188085323 mailed Feb. 15, 2023, with English translation, 29 pages.
Office Action and Search Report for Chinese Application No. CN201980071792.2 dated Sep. 21, 2023, with English translation, 29 pages.
Office Action and Search Report for Chinese Application No. CN20198013115 dated Jul. 17, 2023, with English translation, 25 pages.
Office Action for European Application No. 18875541.7 dated May 9, 2023, 5 pages.
Office Action for Japanese Application No. JP20200537522 dated Jan. 26, 2023, with English translation, 11 pages.
Office Action for Japanese Application No. JP20200537522 dated Oct. 24, 2023, with English translation, 9 pages.
Office Action for Japanese Application No. JP2021515495 mailed Oct. 17, 2023, with machine translation, 9 pages.
Office Action for Korean Application No. KR20207016971 mailed Jan. 24, 2024, with English translation, 21 pages.
Partial Supplementary European Search Report dated Jan. 3, 2018 for European Application No. 15799099.5, 13 pages.
Partial Supplementary European Search Report dated Oct. 15, 2021 for European Application No. 19741853.6, 14 pages.
Perego, P. et al., "Cognitive ability assessment by BrainComputer Interface: Validation of a new assessment method for cognitive abilities," J. Neurosci. Methods, 201:239-250 (2011).
Power, D. et al., "Towards a system-paced near-infrared spectroscopy braincomputer interface: differentiating prefrontal activity due to mental arithmetic and mental singing from the no-control state; Towards a system-paced near-infrared spectroscopy brain-computer interface," Journal of Neural Engineering, 8(6):66004 (2011), 14 pages, doi:10.1088/1741-2560/8/6/066004.
Sakai, Y., et al., Abstract, "A study on the relationship between gazing points and event-related potentials for a P300-based brain computer interface, IEICE Technical Report MBE2012-30-MBE2012-35, ME and Bio Cybernetics", Japan, The Institute of Electronics, Information and Communication Engineers, vol. 112, No. 220, Sep. 20, 2012,4 pages.
Sellers, E. W. & Donchin, E., "A P300-based brain-computer interface: initial tests by ALS patients," Clin. Neurophysiol., 117:528-548 (2006).

(56) References Cited

OTHER PUBLICATIONS

Seo, S. et al., "Discrimination of Yes and No Responses by Auditory Stimuli Multiple-choice Questions in Human EEG," International Conference on Convergence Information Technology, IEEE, pp. 1127-1133 (2007).

Sorger, B. et al., "Another kind of 'BOLD Response': answering multiple-choice questions via online decoded single-trial brain signals ," Progress in Brain Research, Chapter 19, vol. 177, pp. 275-292 (2009).

Thompson, D. E. et al., "Classifier-based latency estimation: a novel way to estimate and predict BCI accuracy," J. Neural Eng., 10(1):016006 (2013), 13 pages, doi:10.1088/1741-2560/10/1/016006. Epub Dec. 12, 2012.

Thompson, D. E. et al., "Performance assessment in brain-computer interface-based augmentative and alternative communication," BioMedical Engineering Online, 12:43 (2013), 23 pages, doi:10.1186/1475-925X-12-43.

Vieru, T., "Brain Computer Interface Can Stimulate the Cortex," Softpedia, Feb. 16, 2010, 4 pages.

Zander, T. O. & Kothe, C., "Towards passive brain-computer interfaces: applying brain-computer interface technology to human-machine systems in general," J. Neural Eng., 8(2):025005 (2011), 5 pages, doi:10.1088/1741-2560/8/2/025005. Epub Mar. 24, 2011.

\* cited by examiner

Score $y_t$ for a stimulus response
$y_t = fv \odot signal$
where fv is feature vector
signal = epoch of reversal signal $$p\left(y_t \middle| x_t\right) \propto \prod_i f\left(y_t^i \middle| x_t^{(L)}\right) \quad \text{—891}$$

$$f\left(y_t^i \middle| x_t\right) = \begin{cases} \frac{1}{\sqrt{2\pi\sigma_a^2}} e^{-\frac{1}{2\sigma_a^2}(y_t^i - \mu_a)^2} & \text{if } x_t \text{ contains target} \\ \frac{1}{\sqrt{2\pi\sigma_a^2}} e^{-\frac{1}{2\sigma_a^2}(y_t^i - \mu_n)^2} & \text{if } x_t \text{ does not contain target} \end{cases}$$

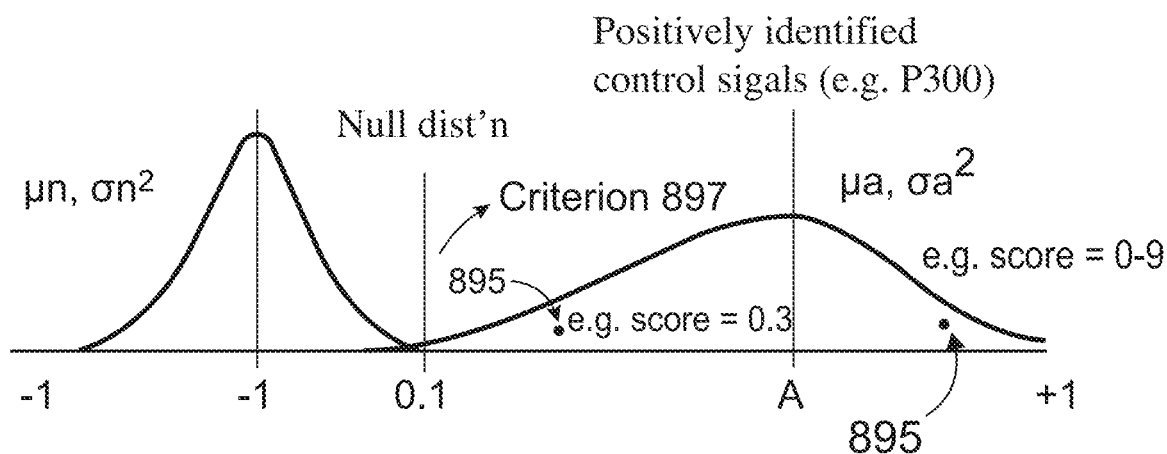

FIG. 8B

BRAIN-COMPUTER INTERFACE WITH ADAPTATIONS FOR HIGH-SPEED, ACCURATE, AND INTUITIVE USER INTERACTIONS

CROSS-REFERENCE TO RELATED APPLICATIONS

This application is a continuation of International Patent Application No. PCT/US2019/014315, entitled "Brain-Computer Interface with Adaptations for High-Speed, Accurate, and Intuitive User Interactions," filed Jan. 18, 2019, which claims priority to and the benefit of U.S. Provisional Patent Application Ser. No. 62/618,846, entitled "Brain-Computer Interface with Adaptations for High-Speed, Accurate, and Intuitive User Interactions," filed Jan. 18, 2018, the disclosures of which are hereby incorporated by reference in their entireties.

BACKGROUND

Embodiments described herein relate to systems, devices, and methods for use in the implementation of a brain-computer interface that integrates real-time eye-movement and/or head-movement tracking with brain activity tracking to present and update a user interface (UI) or a user experience (UX) that is strategically designed for high speed and accuracy of human-machine interaction. Embodiments described herein also relate to the implementation of a hardware agnostic brain-computer interface that uses real-time eye tracking and online analysis of neural activity to mediate user manipulation of machines.

A brain-computer interface (BCI) is a hardware and software communications system that permits brain activity alone to control computers or external devices with direct communication pathways between a wired brain and the external device. BCIs have been mainly designed as an assistive technology to provide access to operating machines and applications directly from interpreting brain signals. One of the main goals of BCI development is to provide communication capabilities to severely disabled people who are totally paralyzed or 'locked in' by neurological neuromuscular disorders, such as amyotrophic lateral sclerosis, brainstem stroke, or spinal cord injury, for whom effective communication with others may be extremely difficult.

Some known implementations of brain computer interfaces include spellers like the one designed by Farwell and Donchin. In this speller, the 26 letters of the alphabet, together with several other symbols and commands, are displayed on-screen in a 6×6 matrix with randomly flashing rows and columns. The user focuses attention on the screen and concentrates successively on the characters to be written, while the neural response of the brain is monitored for signature neural brain signals. Once detected the signature brain signals allow the system to identify the desired symbol. The Farwell-Donchin speller allows people to spell at the rate of about 2 characters per minute.

BCI systems can be designed to assist and enhance even physically able people to operate computers or other data-processing machines and/or software applications without the need for conventional input or output interfaces such as a mouse and a keyboard. BCIs may also provide an interface for more intuitive and natural interaction with a computer than conventional input methods. Additionally, BCIs can also be developed to serve many other functions including augmenting, repairing as well as mapping and researching human and animal cognitive and/or sensory motor systems and their functions. Some BCI applications include word processors, adapted web browsers, brain control of a wheelchair or neuroprostheses, and games, among others.

SUMMARY

Systems, devices and methods are described herein for various embodiments of a hardware-agnostic, integrated oculomotor-neural hybrid brain computer interface (BCI) platform to track eye movements and brain activity to mediate real-time positioning of a user's gaze or attention and selection/activation of desired action. This disclosure presents an integrated BCI system to address the need for Brain Computer Interfaces that operate with high-speed and accuracy.

BRIEF DESCRIPTION OF THE FIGURES

FIGS. 8A and 8B illustrate example analytical methods used to determine a target or tag of user's interest, used in implementing a BCI system, according to an embodiment.

DETAILED DESCRIPTION

Figure 1:
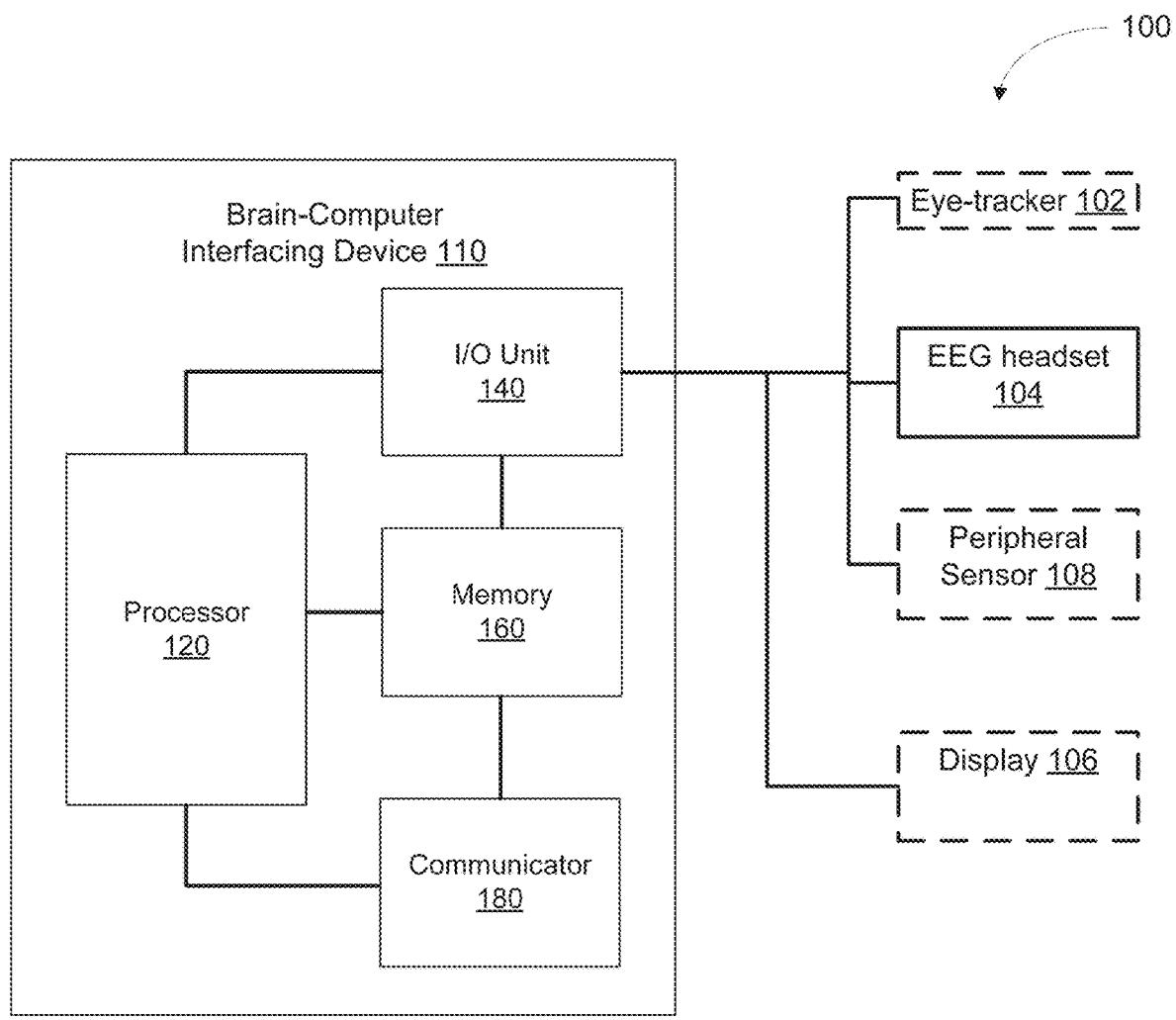
FIG. 1 is a schematic illustration of a hybrid Brain Computer Interfacing system, according to an embodiment.

Embodiments described herein relate to systems, devices, and methods for use in the implementation of a brain-computer interface (BCI) that analyses brain activity recorded while presenting a user with a user interface (UI) or user experience (UX) that is strategically designed for high speed and accuracy of human-machine interaction. Embodiments described herein also relate to the implementation of a hardware agnostic brain-computer interface that uses analysis of neural brain signals to mediate user manipulation of interfaces, devices and/or machines.

For BCI technology to be better suited for patients, useful to the general public, and employed in the control of real-world tasks, the information transfer rate has to be improved to meet a natural interactive pace, the error rate has to be reduced, and the complexity of the interaction interface has to be minimized, compared to current implementations. Additionally, BCI applications demand a high cognitive load from the users, thus the UI/UX and the underlying processing of signals has to be improved to move away from quiet laboratory environments into the real world. In order to configure BCI devices and applications to be easier and more intuitive, there exists a need for improved devices and techniques in the implementation of brain machine interfaces that operate with high-speed and high accuracy to enable user mediated action selection through a natural intuitive process.

A BCI System

As described herein, a BCI is a hardware and software communications system that permits brain activity, alone or in combination with other activities like oculomotor activity or motor neuron (e.g., EMG) activity, to control computers or external devices. A BCI system includes a display of stimuli through an interface, a hardware apparatus to locate the point of focus of a user on the interface, a device for recording and processing brain activity, and an apparatus for effecting control of the interface, which may translate into control over the user's environment. These standard features can be characterized as (1) a pointing control feature, (2) an action control feature, and (3) a user interface/user experience (UI/UX) feature. The pointing control feature can be analogized to a conventional pointing device like a mouse pointer that allows a user to narrow down to a small set of one or more manipulators to control. The action control feature can be analogized to a device that mediates an action (e.g., selection, deselection, etc.), for example a mouse click or a key stroke on a keyboard, that allows the user to implement an action to effect change to the UI/UX and in turn to a connected machine. The UI/UX feature in a BCI system can be analogized to an operating system that creates and maintains an environment that implements the pointing and action control features in addition to other features like offering a selection menu, navigation controls, etc.

The action performed by the action control feature can be one of many and can be adapted to suit various versions of UI/UXs designed to control various devices or machines. To name a few examples, the action can be an activation or a deactivation, a continuous or semi-continuous change to the UI/UX. For example, scrolling, hovering, or pinching, zooming, titling, rotating, swiping, among others. The action can also effect an acute change to the UI/UX with discrete starts and stops like highlighting, etc. Some other examples of action control via a UI/UX can include a virtual keyboard control, a checkbox, a radio button, a dropdown list, a list box, a toggle, a text field, a search field, a breadcrumb navigator, a slider, menu navigation, actions to place and unplace object or items, action to move objects or items, expand and/or shrink objects, movement or navigation of a first person observer or player, changing perspectives of the observer, and actions like grabbing, picking or hovering. Some of these aspects of action control are disclosed below.

In some embodiments of implementing a BCI system, the pointing control feature and methods for identifying a user's point of focus can be implemented through either manipulation of the UI/UX and/or using brain signals that may be informative about the user's point of focus. In some embodiments of a BCI system described herein, the pointing control feature and identifying a user's point of focus can include an eye-movement tracking device and/or a head-movement tracking device or other body-movement or posture tracking devices. In still other embodiments, a combination of brain signals, eye-tracking signals, motor neuron signals such as electromyographic (EMG) signals, and strategic manipulation of the UI/UX can be used simultaneously (e.g., a BCI system) or individually, to implement the pointing control feature. In addition to the above mentioned signals, a BCI system, hybrid or otherwise, can also monitor and use other signals from various peripheral sensors (e.g., head position tracking signals). In some embodiments, a BCI system, hybrid or otherwise, can optionally include an electromyograph (EMG) to record EMG signals that can be integrated in with oculomotor or neural activity signals.

In some embodiments, the action control feature and methods for identifying the intent of the user can include any suitable form of monitoring neural signals in the brain. This can include, for example, brain imaging through electrical or optical or magnetic imaging methods. For example, in some embodiments, the BCI system can use electrodes recording neural signals of brain activity, channeled through an amplifier and a processor that convert the user's brain signals to BCI commands. In some embodiments, the BCI system can implement sophisticated UI/UXs that implement brain activity based control of machines. Specific adaptations to one or more of these features can be implemented, as described below, to achieve high speed and accuracy of human interaction with the BCI system. For example, in some embodiments, the BCI system can be substantially similar to those described in U.S. Patent Application No. 62/549,253 entitled, "Brain-computer interface with high-speed eye tracking features," filed Aug. 25, 2017 ("the '253 application"), the disclosure of which is incorporated herein by reference in its entirety.

The UI/UX can be adapted in consideration with the needs to be met by a BCI system. For example, the BCI system to be used by patients for mobility may include UI/UXs targeting ease of use with low cognitive load. As another example, a BCI system used for children as a learning tool may include UI/UXs tailored for intuitive interaction by children. Similarly, BCI systems intended for a gaming experience can include UI/UX designed for high-speed and accuracy, etc. For example, in some embodiments, the BCI system and/or the user interface/user experience (UI/UX) can be substantially similar to those described in U.S. Patent Application No. 62/585,209 entitled, "Brain-computer interface with adaptations for high-speed, accurate, and intuitive user interactions," filed Nov. 13, 2017 ("the '209 application"), the disclosure of which is incorporated herein by reference in its entirety.

FIG. 1 is a schematic illustration of a Brain Computer Interface system 100, according to an embodiment. The example Brain Computer Interface system 100 (also referred to herein as "hybrid BCI system" or "BCI system" or "system") is a BCI system that includes a neural recording headset 104 (e.g., neural recording device) for recording one or more control signals of the user's brain. The BCI system 100 can also include an eye-tracker 102 (e.g., an eye-tracking device), which can be a video-based eye tracker. The eye-tracker 102 can be an optional accessory or integrated with the BCI system 100. The eye-tracker 102 can be configured to capture, record, and/or transmit oculomotor responses of the eyes of a user indicating the user's point of focus at any time (i.e., the pointing control feature). The neural recording headset 104 can be configured to capture, record and/or transmit neural control signals from one or more brain regions indicating the user's cognitive intent (i.e., the action control feature). In some embodiments, the neural recording headset 104 can be adapted to indicate the user's point of focus implementing the pointing control feature. The neural control signals can be any form of neural activity recorded through any suitable approach, for example, electroencephalography (EEG), electrocorticography (ECoG) or magnetoencephalography (MEG), Intrinsic Signal Imaging (ISI), etc. Example forms of neural activity include Event Related Potentials (ERN), motor imagery, steady state visual evoked potentials (SSVEPs), transitory visual evoked potentials (TVEPs), brain state commands, visual evoked potentials (VEPs), evoked potentials like the P300 evoked potential, sensory evoked potentials, motor evoked, potentials, sensorimotor rhythms such as the mu rhythm or beta rhythm, event related desynchronization (ERDs), event-related synchronization (ERSs), slow cortical potentials (SCPs), etc. The example BCI system 100 can also include a Brain-Computer Interfacing Device 110, one or more optional Peripheral Sensors 108, and optionally an audio-visual display 106. Some embodiments of the BCI system 100, can also include other peripheral sensors 108 and peripheral actuators (not shown in FIG. 1) to collect data about the user's behavior through other modalities like sound, touch, orientation, etc. and to present a rich, multi-modal, user experience.

In some embodiments of the BCI system 100, the neural and oculomotor signals collected from the neural recording headset 104 and the eye-tracker 102, respectively, (and other peripheral signals from the peripheral sensors 108) can be communicated to the Brain-Computer Interfacing (BCI) Device 110 that processes the signals individually or together as an ensemble. In association with the signal processing, the BCI Device 110 can also access and process data about the stimuli that were presented via the UI/UX that evoked the signals processed. With the combined information, the BCI Device 110 can detect relevant signal features based on statistical models, apply suitable confidence scores, as described in further detail below, to predict the user's intent. This predicted intent can then be communicated to the user, via the UI/UX presented through the display 106 for example, and used to effect change in the UI/UX and in any connected controllable machine.

Eye Tracking in Two and Three Dimensional Space—the Pointing Control Feature

In some embodiments, the eye-tracker 102 can be used to determine where a user is looking in their visual field by rapidly following the eye movements of the user in a two or three dimensional space. For example, provided the user has voluntary control of their eye-movements, the video based eye tracer 102 can be used to determine which subspaces in their visual field each of their eyes is "pointing to." In other words, the eye-tracker 102 can use the user's eye-movement trajectories as a pointing control feature, revealing significant information about the subject's intent and behavior. In some embodiments, aspects of where in the visual space their attention focused, what stimulus they are focused upon, or what stimulus they responded to, can be used effectively in the BCI system 100. By simultaneously tracking the movement trajectories of both eyes with respect to each other the eye-tracker 102 can also register the depth of focus of the user, thus enabling pointing control in a three dimensional space.

In some embodiments, the eye-tracker 102 relies on tracking the user's pupil and a first-surface corneal reflection (CR) of an illumination source with the use of a head-mounted eye tracking video camera to image the user's eye. The positional difference between these two features can be used to determine the observer's eye-in-head orientation. Some example head mounted eye-tracking devices that can be used as the eye-tracker 102 are available from SenseMotoric Instruments, Tobii Eye Tracking, and Pupil-labs among other commercial vendors. In some embodiments, the eye-tracker 102 can include one or more illumination sources illuminating the eyes of a user. The illumination sources can be emitting light of any suitable wavelength and be mounted at any suitable position. The illumination sources can be connected through wired or wireless communication for function control and transmission of data, etc.

The eye-tracker 102 can include a left and a right eye camera each configured to simultaneously image the pupil and the conical reflection of the one or more illumination sources, from each eye. The cameras can be connected to each other, and connected to an external device like the Brain-Computer Interfacing (BCI) Device 110 shown in FIG. 1, through a wired or wireless connection. The eye-tracker can also include an additional scene camera that captures the user's field of view. The signals from the scene camera can also be relayed through wired or wireless communication methods to the external device like the BCI Device 110.

In some embodiments, the eye-tracker 102 can include an integrated display 106 instead of the separate display 106. For example, an eye-tracker 102 integrated with a display 106 can be a system configured to view virtual reality space. In some embodiments, the eye-tracker 102 integrated with a display 106 can be configured to view augmented reality space. That is, functioning to view the real-world as a pair of eye-glasses with the addition of a superimposed UI/UX presented through the display 106.

Neural Recording of Brain Signals—the Action Control Feature

The purpose of the BCI system 100 is to actively control an associated UI/UX and/or connected external devices and/or machines by determining user intentions from monitoring cerebral activity, such as, for example, predicting an action intended by a user and/or interpreting signals associated with user activity to determine an action intended by the user. Central to this purpose are brain signals that can be indicative of the user's intent, making the brain signals an action control feature. The BCI system 100 can use one or more of several signature brain signals simultaneously evoked by or related to cognitive tasks performed by a user. Some of these brain signals can be decoded in ways that people may learn to modulate them at will. Using these signals, regarded as control signals, can enable the BCI system 100 to interpret the intentions of the user.

The neural recording headset 104 can be adapted to record neural activity, generated by electro-chemical transmitters exchanging information between the neurons, using any suitable approach. Neural activity can be captured directly by electrically recording the primary ionic currents generated by neurons, the ionic currents flowing within and across neuronal assemblies. Neural activity can also be captured indirectly by recording secondary currents or other changes in the nervous system, associated with or resulting from the primary currents. For example, neural activity can also be monitored through other methods like optical imaging (e.g., functional magnetic resonance imaging, fMRI), by the recording optical changes that are consequent to the primary currents. Other approaches to recording neural activity of the brain include electroencephalography (EEG), electrocorticography (ECoG), Functional Near-Infrared (FNIR) Imaging and other similar Intrinsic Signal Imaging (ISI) methods, magnetoencephalography (MEG), etc.

A variety of signature brain signals in the form of neural activity can be used as a control signal used for implementing the action control feature. Some examples of neural activity in time include Event Related Potentials (ERPs), Evoked Potentials (EPs e.g., sensory evoked potentials, motor evoked potentials, visually evoked potentials), motor imagery, slow cortical potentials, a sensorimotor rhythm, an event related desynchronization (ERD), an event related synchronization (ERS), a brain state dependent signal, and other, as yet undiscovered, signature activity potentials underlying various cognitive or sensorimotor tasks. Neural activity can also be the frequency domain. Some examples among others include sensorimotor rhythms, Event Related Spectral Perturbations (ERSPs), specific signal frequency bands like Theta, Gamma or Mu rhythms, etc.

As described herein, the neural recording headset 104 can record neural activity signals to gather information on user intentions through a recording stage that measures brain activity and translates the information into tractable electrical signals that can be converted into commands. In some embodiments, the neural recording headset 104 can be configured to record electrophysiological activity through electroencephalography (EEG) which has a high temporal resolution, low cost of set-up and maintenance, high portability, and is non-invasive to users. The neural recording headset 104 can include a set of electrodes having sensors that acquire electroencephalography signals from different brain areas. These sensors can measure electrical signals caused by the flow of electric currents during synaptic excitations of the dendrites in the neurons thereby relaying the effects of secondary currents. The neural signals can be recorded through the electrodes in the neural recording headset 104 appropriately arranged over desired brain areas when placed over the head, scalp, face, ears, neck, and/or other parts of a user. Example neural recording headset may be available from commercial vendors like Biosemi, Wearable Sensing and G.Tec among others. For example, in some embodiments, the neural recording headset 104, its operation in gathering neural brain activity signals, and signal transfer from the neural recording headset 104 can be substantially similar to those described in the '253 application, the disclosure of which is incorporated herein by reference in its entirety above, and/or those described in the '209 application, the disclosure of which is incorporated herein by reference in its entirely above.

The neural activity recorded and analyzed to decode user intentions can be any form of a control signal indicating the user's intent. One example of a control signal can be an Event Related Potential (e.g., a P300 signal). An Event Related Potential or an ERP can be a signature neural activity related to an event or a stimulus presentation correlated in time. ERPs can have distinct shape and features (like the P300 signal known to peak at around 300 ms following the triggering stimulus) that helps with their detection and identification. ERPs can also vary in size and shape across different brain regions and how they map across brain regions can be indicative of specific brain functions and/or user intentions. The neural activity data acquired from the neural recording headset can be analyzed for specific ERP signals and once detected and classified appropriately the BCI Device 110 can implement any particular action associated with the detected ERP on the desired portion of the UI/UX.

Another example control signal can be the form of Motor Imagery signals which are neural activity signals associated with the user undergoing the mental process of motion. That is, motor imagery signals are brain signals that can be recorded from various brain regions and analyzed by a BCI system 100 while the user imagines the action and/or performs the action. The BCI system can also use information gathered by peripheral sensors 108 like goniometers and torsiometers to help recognize the gesture in high detail during a training session.

Display and Presentation of the UI/UX

As described herein, the UI/UX in the BCI system 100 functions as a link of communication between the user (e.g., the user's brain, eyes, muscles/motor neurons, etc) and the BCI Device 110, and enables a user to focus and point at specific stimuli through the pointing control feature and select or deselect specific stimuli using the action control feature. As referred to herein, the UI/UX can be an example of a control interface. The UI/UX can include a sequence of visually stimulating two dimensional images, presented via a display. The UI/UX can be designed and manipulated by a BCI Device 110 to be presented in a manner that is most intuitive for the user and that makes the identification of the user's intent easier and unambiguous. The UI/UX can present one or more stimuli that are designed to capture a user's attention and/or convey information about the UI/UX including information about the availability of a method of user control. A stimulus can be presented in any suitable manner. For example, the UI/UX can be designed to present "tags" (e.g., control items) as stimuli. Each stimulus can include one or more tags. For example, tags can be visual icons that change their appearance in specific manner to catch the attention of a user and to indicate their usability to control the UI/UX. For example, a group of one or more tags can be made to flash or change their appearance in a specific manner. Tags or control items can be associated with actions. For example, the transient change in appearance of tags, also referred to herein as a "tag flash" can indicate that they can be used to perform one or more specific actions. More than one tag can be flashed at a time, with the grouping of tags (also referred to as a "tag-group") made in any particular manner (e.g., rows, columns, pseudorandom grouping of tags, etc.). Following the tag flash, the eye-tracker 102 can capture signals that indicate that the user foveated to the position of the tag flash and/or the neural recording headset 104 can capture signals indicating the occurrence of a signature brain activity. The BCI Device 110 can analyze these signals, as described in further detail herein, and determine the intent of the user. Based on this determination, the UI/UX can implement the one or more specific actions associated with the tag flash.

As described above, the UI/UX can also be a rich mixture of stimuli in several modalities, together forming what can be called a user experience (UX) that also acts as an interface (UI). A strategically designed user experience includes a process of presentation of stimuli to a user through any modality, as described above with respect to the user interface, manipulating the presentation (similar to a tag flash). Upon analyzing the brain activity signals and associated eye-movement and/or other peripheral signals, and decoding the user's intent, the UI/UX can implement the one or more specific actions associated with the presented stimuli.

Some examples including visual stimuli, auditory stimuli, haptic stimuli or vestibular stimuli. In some embodiments, a UI/UX that presents visual stimuli can be rendered on a display like the display 106 shown in FIG. 1. The stimuli of other modalities can be delivered though suitable peripheral actuators (not shown in FIG. 1) also being a part of the BCI system 100.

In some embodiments, the display 106 can be a separate, stand-alone, audio-visual display unit that can be connected and in data communication with the rest of the BCI system 100. That is, a stand-alone display (e.g., a liquid crystal display) equipped with an audio system (e.g., speakers, or headphones) can be in two-way communication with one or more of the other components of the BCI system 100, for example, the BC Interfacing Device 110, the eye-tracker 102, and the neural recording headset 104. In some embodiments, the display 106 can be integrated into the eye-tracker 102 to be part of the eye-glass area. The integrated eye-tracker 102 and display 106 can be configured to view virtual reality space in the form of a UI/UX presented on the display 106. In some embodiments, the integrated eye-tracker 102 and display 106 can be configured such that the display 106 is on a semi-transparent eye-glass area, allowing the user to view augmented reality space. That is, the user can view the real-world through the semi-transparent eye-glass area that is also the integrated display 106 presenting the user with a UI/UX that he/she can interact with.

Peripheral Devices Operating in Non-Visual Modalities

In some embodiments, the BCI system 100 can include several peripheral sensors 108 (shown as optional units indicated by the dashed boxes in FIG. 1) and peripheral actuators (not shown in FIG. 1). The one or more peripheral actuators can be configured to deliver a rich multi-modal user experience and the one or more peripheral sensors 108 can be configured to capture multimodal input from the user and his/her environment, respectively. These peripheral actuators 112 and sensors 108 can be suitably mounted either individually or by being incorporated into other devices (like the eye-tracker 102). For example, the BCI system 100 can include earphones to relay auditory stimuli and microphones to capture sounds like the user's voice commands. The earphones (auditory actuators or auditory output device) and the microphones (auditory sensors or auditory input device) can be either stand-alone devices connected through wired or wireless channels to the hybrid system 100. Alternatively, they can be mounted and integrated with the eye-tracker 102 or the neural recording headset 104. Similarly, peripheral sensors like accelerometers, goniometers, torsiometers, light sensors such as infrared cameras, depth sensors, microphones, etc. can be included in and/or coupled to the BCI system 100 to register body movements. For example, goniometers can be used register limb movements forming gestures, accelerometers can be used to register body movements. Peripheral sensors can also include a visual field camera configure to capture the real-world visual field of the user. The signals acquired by the visual field camera can be analyzed and used to generate and present the user with an augmented or mixed reality experience having real-world imagery superimposed by UI/UXs with selectable options, etc. Peripheral actuators that can be connected to a BCI system 100 can include haptic or kinesthetic devices that can apply and create forces like touch and vibration enriching the user experience presented.

The Brain-Computer Interfacing Device

In some embodiments, the Brain-Computer Interfacing Device (or BCI Device) 110 can be configured to accomplish three main functions among others. First, the BCI Device 110 can be configured to generate a strategically designed UI/UX as described herein. For example, the strategically designed user experience can be for a training session or for a testing session. In some embodiments, the user experience can be designed as a virtual reality environment and/or as an augmented reality environment. In some embodiments, the UI/UX can be tailored for specific needs such as, for example, specific user history, reaction times, user preferences, etc. The BCI Device 110 can account for all these requirements in the generation and updating the UI/UX. Second, in addition to designing and generating the UI/UX, the BCI Device 110 can be configured to receive the pointing control signal (e.g., from the eye-tracker 102) and the action control signal (e.g., from the neural recording headset 104) (and peripheral signals from peripheral sensors 108, if applicable) and process the signals individually or as an ensemble to determine the user's intent. The BCI Device 110 can carry out any suitable method for analysis. For example, the BCI Device 110 can detect meaningful features from the signals, build and apply statistical models to interpret the signals, classify the signals, score the signals and the stimuli evoking the signals, compute probability of any given tag or stimulus being the point of user's intent (e.g., a target tag or target stimulus), determine the target tag or target stimulus and the associated action desired by the user, etc. Thirdly, the BCI Device 110 can be configured to implement the pointing control feature and the action control feature by implementing changes to the target tag or target stimulus being pointed to per the user's intent.

In some embodiments, the BCI Device 110 can also be connected to other peripheral devices, for example, peripheral sensors and actuators functioning in modalities other than the visual modality as mentioned above, that may be a part of the BCI system 100. Such peripheral sensors may include audio microphones, haptic sensors, accelerometers, goniometers, etc., and peripheral actuators can include audio speakers, haptic stimulus providers, etc.

In some embodiments, the BCI Device 110 can include an Input/Output Unit 140 configured to receive and send signals to and from the BCI Device 110 to one or more external devices through wired or wireless communication channels. For example, the Input/Output Unit 140 can receive signals from and send signals to the eye-tracker 102, the neural recording headset 104, and the optional audio visual display 106 through one or more data communication ports. The BCI Device 110 can also be configured to be able to connect to remote servers (not shown in FIG. 1) and access databases or other suitable information contained in remote servers. The BCE Device 110 can include a Communicator 180 configured to handle suitable channels of communication adapting to the type of data to be transferred. The Communicator 180 can be connected to the I/O Unit 140 among other parts of the BCI Device 110 and control the functions of the Input/Output Unit 140. The transfer of signals can also be carried out through a wired connection like wired Ethernet, Serial, FireWire, or USB connection, or wirelessly through any suitable communication channel like Bluetooth, Nearfield communication, etc.

In some embodiments, the functions of the Input/Output Unit 140 in the BCI Device 110 can include several procedures like signal acquisition, signal preprocessing and/or signal enhancement, etc. The acquired and/or pre-processed signal can be channeled to a processor 120 within the BC Interfacing Device 110. In some embodiments, the processor 120 and its sub-components (not shown) can be configured to handle the incoming data, send and retrieve data to and from a memory 160. The processor 120 can also be connected to the communicator 180 to access and avail information from remote servers (not shown in FIG. 1).

The processor 120 in the BCI Device 110 can be configured to carry out the functions of building and maintaining a UI/UX which can be rendered on the display 106 or on a display integrated with the eye-tracker 102. In some embodiments, the processor 120 and its sub-components can be configured to carry out the functions needed to enable user-specific interpretation of brain signals, and packaging output signals to the Input/Output Unit 140 to be relayed to external devices. Other functions of the processor 120 and its sub-components can include several procedures like feature extraction, classification, and manipulation of the control interface.

In some embodiments, to improve user experience, BCI Device 110 can be configured to optimize for speed, such that the implementation of the action control occurs within 5 seconds, or within 4 seconds, or within 3 seconds, or within 2 seconds, or within 1 second, or within 0.9 seconds, or within 0.8 seconds, or within 0.7 seconds, or within 0.6 seconds, or within 0.5 seconds. In some embodiments, to improve user experience, BCI Device 110 can be tuned to reduce or minimize a value of speed*accuracy %, such that the implementation of the action control speed (in seconds) times the average accuracy of the system (in %) is less than 5 (e.g., 10 s*50% accuracy), or less than 4, or less than 3, less than 2, or less than 1.125 (e.g., 1.5 s*75% accuracy), or less than 1, or less than 0.9 (e.g., 1 s*90% accuracy), or less than 0.8, or less than 0.7, or less than 0.6, or less than 0.5 (e.g. 0.6 s*83.33% accuracy), or less than 0.4, or less than 0.3, or less than 0.2, or even less than 0.1.

Pointing to and Selecting an Action—Working of a BCI System

Figure 2:
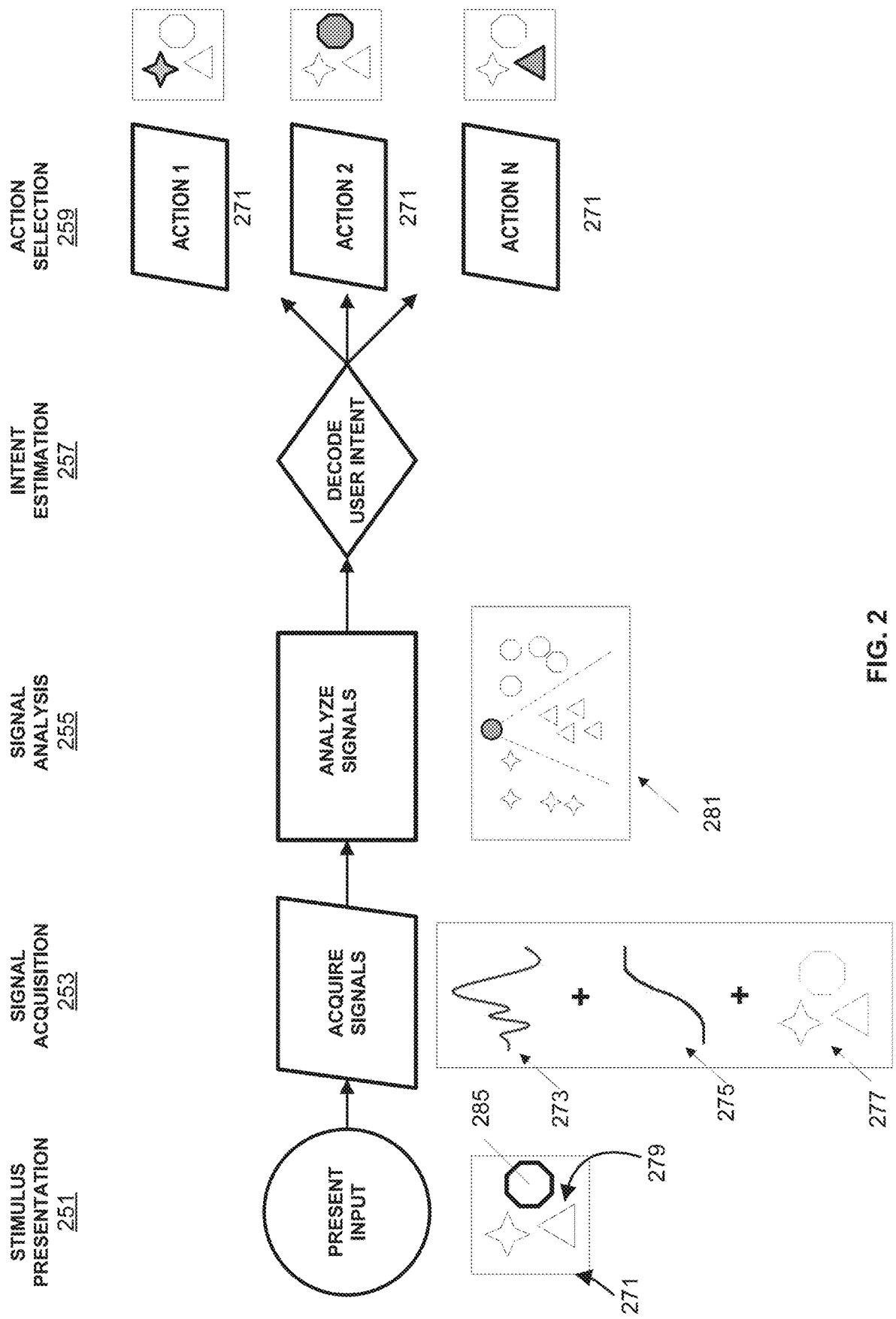
FIG. 2 is an illustration of the sequence of steps in an example implementation of a pointing control feature and an action control feature to select/deselect one stimulus icon, using an embodiment of the BCI Device.

FIG. 2 shows, the working of a BCI system (similar to the system 100 described above) for one example instantiation of a user focusing on and controlling the selection of an example input symbol. The illustrative example sequence of operational events in FIG. 2 includes presentation of a stimulus (e.g., stimulus including a set of tags associated with a set of actions), acquiring ensuing neural activity signals and oculomotor signals and/or peripheral signals if applicable, analyzing the signals acquired, interpreting these signals to deduce or decode the user's intent, and effecting change in the UI/UX (e.g., by selecting one or more of the tags associated with one or more of the actions). The one or more actions implemented to change the UI/UX can in turn also control one or more external machines connected via the UI/UX.

The instance of working of the BCI system illustrated in FIG. 2 begins at step 251 with the presentation of an input stimulus. The input stimulus can be, for example, a set of tags or symbols 279 shown in an example UI/UX 271. While all the tags 279 in the UI/UX 271 may be visible, one or more of the tags 279 can be made to transiently change in visual appearance to indicate their usability for selection. The change in appearance can be a change in any suitable property of the tags (e.g., fill, transparency, intensity, contrast, color, shape, size, orientation, texture, hue, outline, location, depth in 3D environment, mobility, etc.). For example, one or more of the tags 279 can be made to flash (otherwise referred to herein as a. "tag flash") to indicate a potential selection. Different groupings of the visible tags 279 can be made to flash together resulting in several combinations of tag flashes, or several of tag-group flashes, each tag flash or tag-group flash being a stimulus. It should be noted that while the example stimuli are described to be in the visual modality and changes are presented in the visual modality, any suitable modality can be used to present stimuli and carry out similar action selection. For example, auditory tones can be used as tags. Any suitable auditory property of the auditory tags can be transiently changed to indicate their availability to be selected. For example, properties like loudness, duration, pitch, chirp, timbre, etc. can be transiently changed to be used as tag flashes in the auditory space of the UI/UX.

The various tags presented, for example, the three symbols 279 in the UI/UX 271, can each be mediate a distinct action when selected. One of the visible tags can be the target tag or the tag that a user wants to select. The goal of a BCI system (like the BCI system 100 described above), through the example procedure illustrated in FIG. 2, is to determine which of the visible tags 279 is the target tag that the user wants to select.

The UI/UX 271 can be configured to present each visible tag 279 one or more times as a stimulus (by tag flashing, for example) at step 251 and at step 253 the BCI system (e.g., system 100) acquire the ensuing brain activity signal 273 and/or the eye-movement signal 275 and other peripheral sensor signals (not shown) along with information about stimulus presentation 277 (e.g., which tag or tag-group was presented, at what time point, at what location of the UI/UX 271, etc.), as applicable. The visible tags 279 can be presented through tag flashing singly or in combinations of tag-groups. Tag flashing in tag-groups can reduce the number of flashed required to locate the target tag 285. Stimulus presentation can also include pseudo presentation of invisible stimuli, of ghost flashes that are not tied to a tag, that are expected to be unnoticed by the user. Ghost flashes can be used to calibrate the stimulus presentation by the UI/UX 271. For example, ghost flashes can be used to set detection thresholds during analysis of signals indicating the user's focus or attention on a particular tag 279.

Step 255 of the procedure described in FIG. 2 includes analysis of the acquired oculomotor signals 275 and/or neural signals 273 (and other peripheral signals from other sensors) which can be carried out individually or as an ensemble in an integrated approach as further disclosed below. The analysis of signals neural and oculomotor (and peripheral) signals is performed in the context of stimulus information 277 (for example, the spatiotemporal properties of the presented stimulus). The analysis can include one or more steps of several computational methods. For example, pre-processing of the signals, feature detection and feature extraction, dimensionality reduction, supervised, unsupervised or semi-supervised classification, building or applying one or more pre-built statistical model to interpret signals, computation of a confidence score of each analysis (e.g., confidence score of the classification), computation of a suitable manner to incorporate and use stimulus information 277 (e.g., application of one or more scaling functions), computation of likelihood of each tag 279 being the target tag 285, decoding and/or decision making regarding the determination of the identity of the target tag 285, etc.

For example, the step 257 can include determination of the identity of the target tag 285 based on the analyses carried out at step 255. The decision or determination at step 257 can be carried out using any suitable method. For example, using one or more threshold crossing algorithms, or Machine Learning tools.

The decision at step 257 can lead to the selection of one of the tags 279 in step 259. The selection in step 259 can in turn lead to the associated action being performed. For example, if the target tag 285 is correctly identified to be the octagon tag, the action 2 associated with the octagon can be performed. One or more step of user verification can also be included to ascertain whether the identification of the target tag 285 was correct. The user can give a feedback on whether the identification of the target tag 285 was tight or wrong. This user feedback can be used to affirm or correct the various analytical processes and statistical models used for the determination of the target tag 285 training the BCI system to be a better match for a particular user or a particular use case, etc. The feedback can also be used to train the user. For example, if the information to make the decision at 257 is not sufficient, for example, due to ambiguity, or because one or more signals is too weak, the user can be provided with an indicator to try again wider different circumstances (e.g., better focus)

User Interaction with the BCI System

Figure 3A:
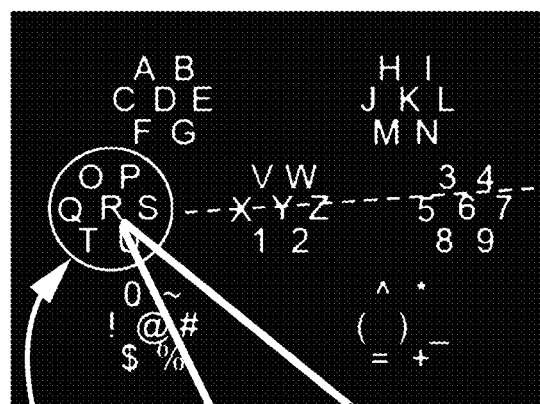
FIGS. 3A, 3B, and 3C show the UI/UX while presenting options, after implementing the pointing control feature, and after implementing the action control feature, respectively.
Figure 3B:
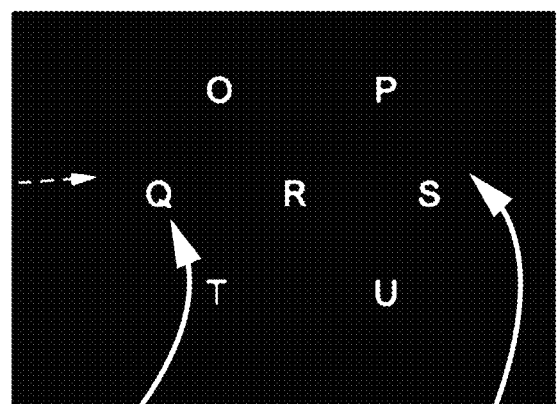
Figure 3D:
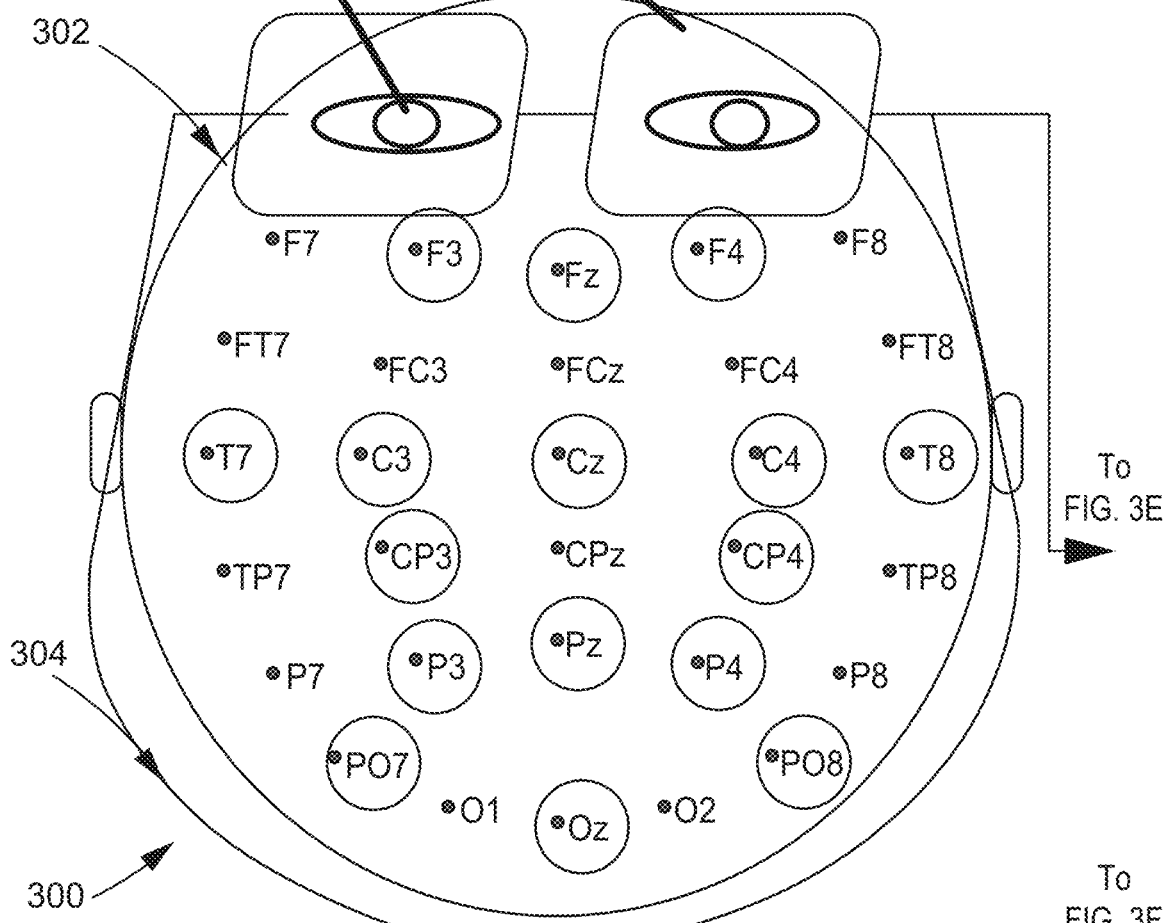
FIG. 3D illustrates a user mounted with an eye-tracker and a neural recording headset, according to an embodiment.
Figure 3C:
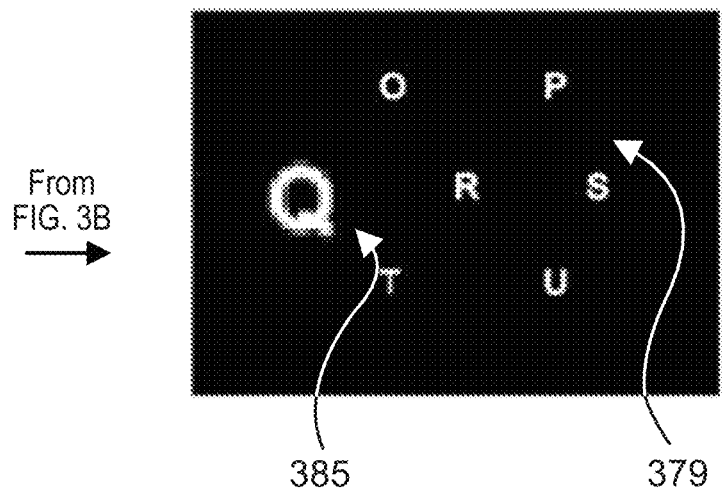

FIGS. 3A-3G illustrates an example user interaction with and some of the underlying processing within a BCI system 300, which can be the same or similar in structure and or function to the BCI system 100 disclosed above. For example, the BCI system 300 can include an eye-tracker 302, a neural recording headset 304, a BCI Device (not shown) and a display 306. In the example illustrated, the BCI system 300 can use both oculomotor signals implementing pointing control as well as neural signals implementing action control to help users spell words and/or sentences. For example, the BCI system 300 can include a UI/UX 371 used to spell words in a two-step process, and a display 306 presenting the UI/UX 371, The UI/UX 371 can present stimuli in the form of tag-group flashes 379 (e.g., letters, numbers and symbols commonly found on a keyboard) as shown in FIGS. 3A-3C.

Figure 3E:
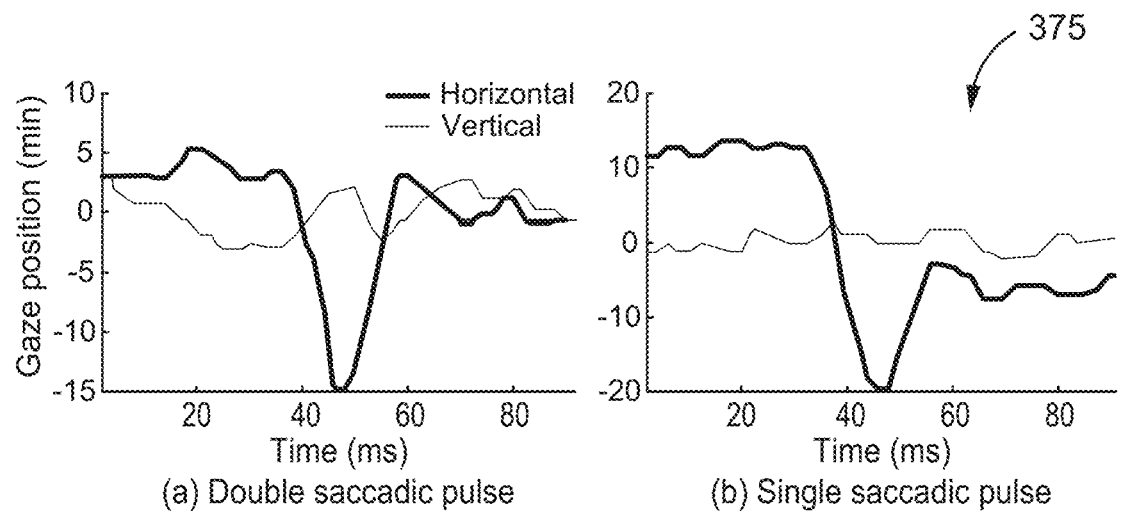
FIGS. 3E and 3F show example signals acquired by the eye-tracker and the neural recording headset shown in FIG. 3D.
Figure 3F:
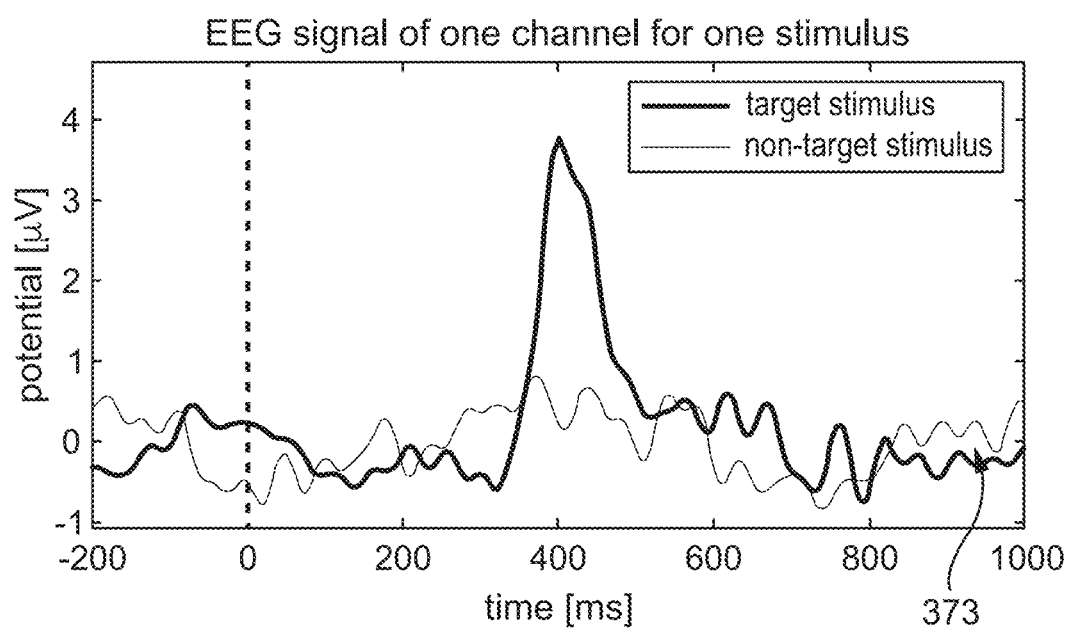

The pointing control feature described with reference to FIGS. 3A-3C, can be implemented with data acquired by the eye-tracker 302 (an example shown in FIG. 3D), The eye-tracker 302 can be configured to record oculomotor signals to detect where the user is focusing their gaze, and output signals corresponding to each eye which can be processed by a BCI Device (not shown). Example oculomotor signals are shown in FIG. 3E. The action control feature (i.e., determination of the target tag and activation of the target tag) is implemented with the data recorded by the neural recording headset 304 (an example of which is shown in FIG. 3F). The neural recording headset 304 can be configured to record neural signals from specific regions in the user's brain, and a BCI Device (not shown) can analyze the signals, examples of which are shown in FIG. 3F. A BCI Device (not shown) can extract meaningful features from the oculomotor signals (FIG. 3E) and the neural signals (FIG. 3F) and analyze them either in an unsupervised and/or semi-supervised manner or by classifying the signals based on statistical models built through training. The BCI Device can incorporate stimulus information in determination and selection of the target tag 385.

For example, the user can focus their gaze on a tag-group containing the target tag (e.g., the letter Q) as indicated in FIG. 3A. In this example the tag-group flash can be in the form of the highlighted circle. As shown in FIG. 3B the tag-group indicated by the highlighted circle in FIG. 3A can be magnified following the analysis of oculomotor signals indicating that the user focused on that specific tag-group, changing the UI/UX 371 to that shown in FIG. 3B. A different set of tag flashes 379 from the magnified group in FIGS. 3B and 3C can then be presented sequentially for the user to select. The tag flashes can be magnification or bolding of the letters as shown in FIG. 3C.

Figure 3G:
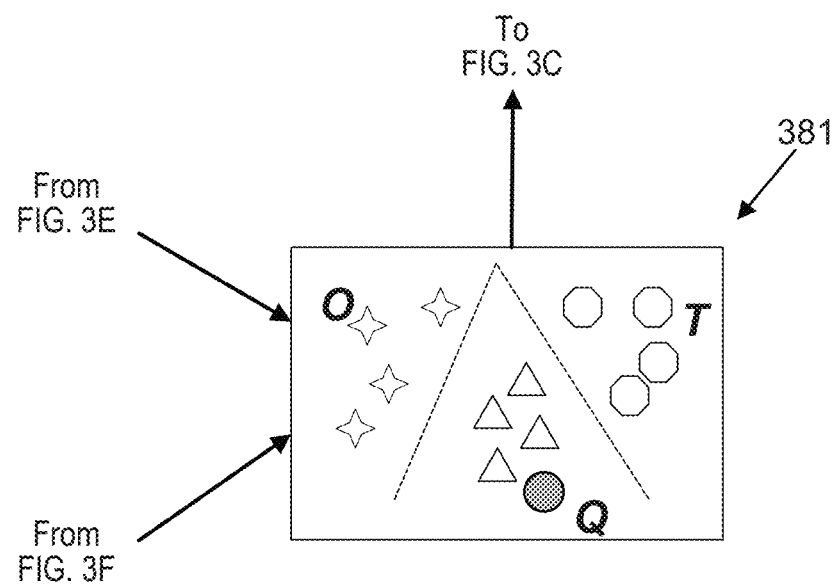
FIG. 3G is an illustration of a signal analysis by an example classifier used in a BCI Device, according to an embodiment.

The target tag 385 can be selected following appropriate analysis of oculomotor signals, neural signals and/or other associated signals, as shown by an example projection 381 of signals used for classification (shown in FIG. 3G). The above described BCI system 300 and implementation procedure can be used to spell words and/or sentences by repeating this procedure for the selection of each letter to be used.

Neural Signal Decoding

Figure 4:
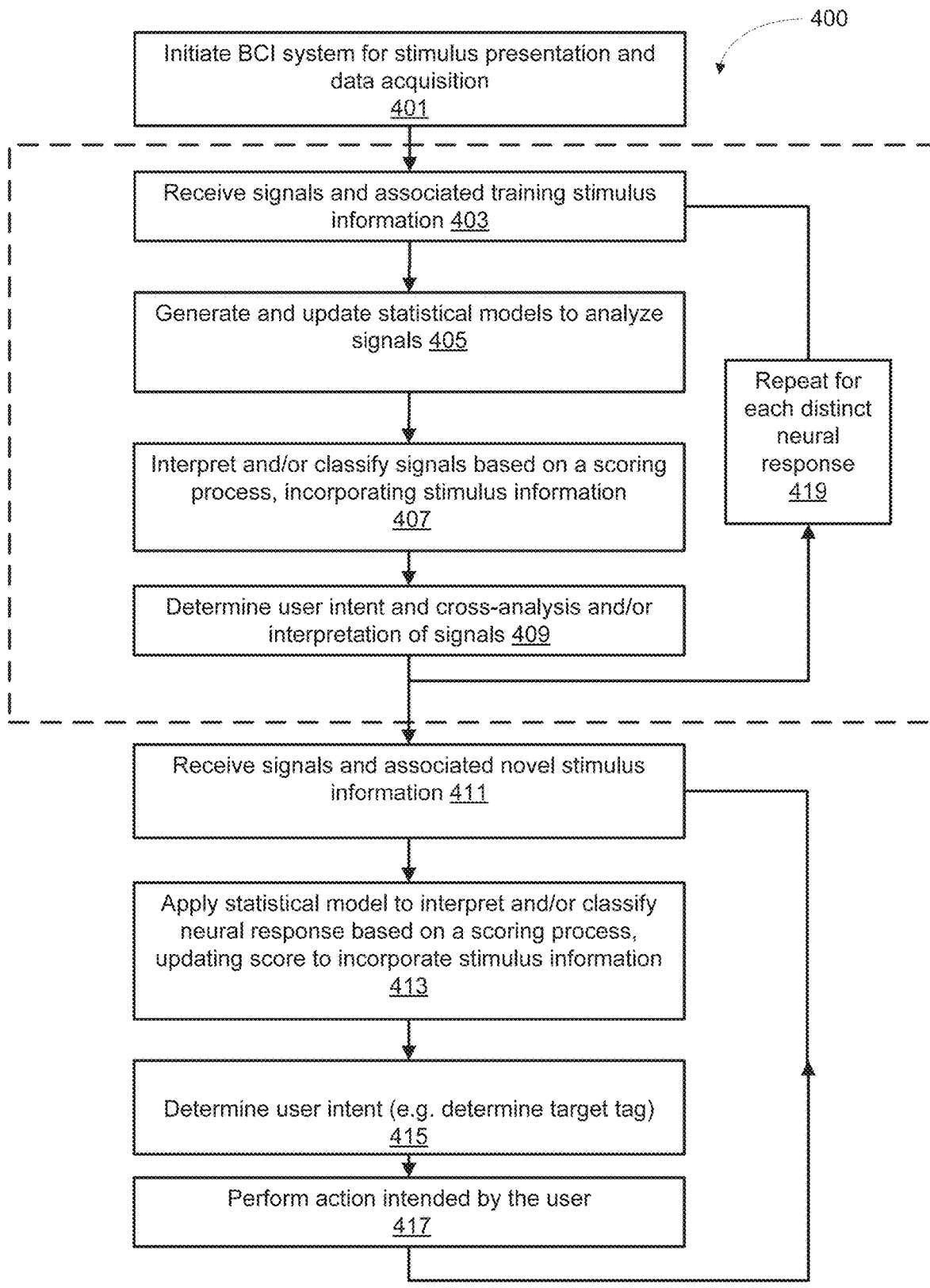
FIG. 4 shows an example operational flow followed by a processor in a Brain Computer Interfacing Device to determine a user's intent, according to an embodiment.

While the process sequence illustrated in FIG. 2 and the example pointing control and action control implementation shown in FIG. 3 can be instantiated for an individual stimulus, a similar process with a similar sequence of steps can be followed during the presentation of virtual or augmented, multimodal, environments via a UI/UX or user experience. An example process 400 is shown in FIG. 4. As shown in FIG. 4 the process 400 can include a sequence of sub-steps that form a training session (indicated as optional by a box with dashed lines) or can be used for presentation of new stimuli without any training data.

The example process 400 shown in FIG. 4 describes some of the steps involved in interpreting recorded signals, determining user intent and acting upon the user intent. The process 400 includes an initial step 401 of initiating a BCI system with timed data acquisition and presentation of a UI/UX for a particular user associated with the system including an eye-tracker and/or a neural recording headset (and other peripheral sensors and/or actuators) at a given time-point. This initiation of stimulus presentation and signal acquisition can be carried out by components that are a part of a BCI system similar to the BCI system 100 or 300 described above.

The process 400 can include a sub-set of steps (optionally used for training sessions, indicated within the dashed box in FIG. 4) for the purpose of generation of and training of a statistical model. Following presentation of a training stimulus (that may be associated with a training environment), the sub-set of steps for the training session can include a step 403 of receiving the acquired signals and information about the training stimulus presented to the user. In step 405 the BCI system can analyze the acquired signals through any suitable analytical procedure. For example, by detecting and extracting specific informative features in the signals, and/or by building/applying one or more statistical models accounting for the oculomotor and/or neural (and/or peripheral) signals. At step 407 the BCI system can interpret, classify, and/or label the acquired signals using any suitable method. For example the BCI system can associate each signal with a classified group and a confidence score measuring the degree of confidence in the classification. The step 407 can also include updating the classification and/or label with information regarding the stimulus presented (e.g., distance scaling methods described further in detail below). At step 409, the BCI system can include a Cross-validation step to evaluate the analytical tools used to interpret the signals and to determine user intent.

Either following a training session or without a training session a user can be presented with stimuli through a UI/UX or user experience following initiation of data acquisition in step 401. These new stimuli can evoke oculomotor, neural and/or peripheral responses captured as signals by appropriate sensors of the BCI system. These signals can be received in association with information about the stimulus that evoked the responses, as is shown in step 411 of the process 400. At step 413, the BCI system can generate a new statistical model or use a pre-generated and cross-validated statistical model from training. Using the statistical models the BCI system can analyze and interpret the signals following analytical procedures similar to those described with respect to step 405 and 407. For example, the BCI system can classify and/or label the signals based on a scoring system, incorporating stimulus information in the scoring system. Based on the score associated with each available stimulus and/or response signal, at step 415, the BCI system can determine the user's intent (e.g., identify the target tag of interest to the user). At step 417 the BCI system can implement the selection of the determined target tag which can result in one or more actions associated with the target tag selection. For example, the step 417 can include selection of a letter in a speller, or selection of a character in a game, or the selection of ON functionality associated with a TV system that can be operated in an augmented reality system, etc.

Signal Analysis

As described herein, the BCI systems 100, 300 can process oculomotor and neural activity signals (and other peripheral signals), in conjunction as an ensemble or individually, to determine and act upon a user's intent, with high speed and accuracy. One or more processes like the process 200 or the process 400 can be used to present appropriate stimuli and determine the user's intent. The BCI system can adopt a suitable analytical pipeline for the analysis of signals and determination of user intent, as described below.

Some embodiments of the BCI system and/or processes of implementing the BCI system can, for example, use an integrated approach to implementing the pointing control feature and the action control feature using complementary sources of information from the various signals received and processed (e.g., oculomotor signals, neural signals, peripheral signals, etc.) Furthermore, an integrated approach of processing the signals and implementing a BCI interface can allow the appropriate weighting of the individual signals according to other parameters like use circumstances, user history and specific details of the UI/UX navigated, etc.

An example analytical pipeline for analyzing signals (e.g., neural activity signals, oculomotor signals, etc.) to determine a user's intent can include: (1) suitable pre-processing of one or more of the signals through one or more filtration systems (e.g., a dual kalman filter, or any other lagless filter), (2) a Bayesian linear discriminant classifier to classify events registered in significant epochs of the signals (e.g., epochs following or concurrent with a stimulus or tag flash), (3) spatial filtering over the weighted signal package, (4) a bagging ensemble classifier algorithm, and (5) a higher-order oracle algorithm that incorporates information from the classification algorithm with program routines during the experimental task, to improve selection accuracy.

Stimulus—Response Relationship

Figure 5A:
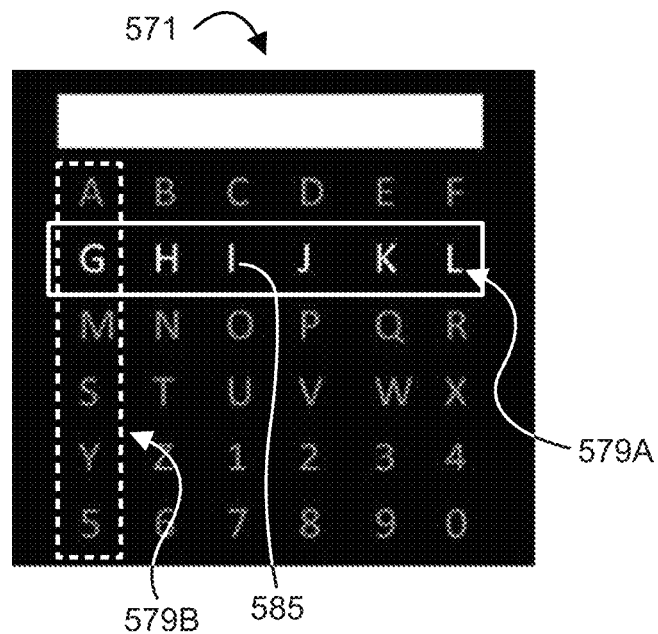
FIG. 5A illustrates an example UI/UX of a BCI system, a speller, presenting an example stimulus group (e.g., tag-group flash).
Figure 5B:
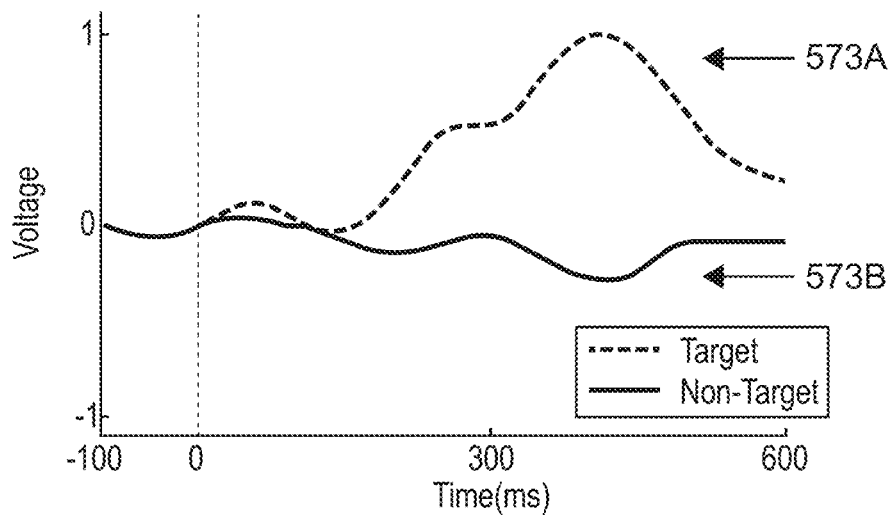
FIG. 5B shows example neural signals acquired in response to the presentation of stimulus (or tag-group) with and without including a target tag or stimulus intended by a user, using a BCI system according to an embodiment.

Signals acquired during and following the presentation of a stimulus, including oculomotor, neural or other peripheral signals (e.g., gesture, posture, voice command, etc.) can be rich in information. Analytical procedures however can extract relevant epochs and/or features from the signals to analyze and determine a target tag. For example, a BCI system can include a UI/UX 571 is shown in FIG. 54 for use in spelling words. In an instance where a user may want to use the letter I to spell a word, the letter I becomes the target tag 585, as shown in FIG. 5A-5B. In the example illustrated in FIG. 5A an example stimulus or a tag flash can be a row or column of the visible tags or letters. For example, an example tag flash 579A presented a stimulus in the form of a highlighted tag-group including the row of tags G-L. Another example tag flash 579B (not presented currently, e.g., letters not highlighted) can include the tags A, G, M, S, Y, and 5. Tag flashes can be rows, columns, or arbitrarily selected tag-groups presented together through a specific change in appearance (e.g., by highlighting, magnifying, boldening, etc.).

Neural activity signals acquired during presentation of one or more stimuli can include specific identifiable signature events or responses called control signals. Signature neural responses or otherwise called control signals are specific brain activity signals that can be associated with a user's cognitive intent, as described herein. Therefore, the occurrence of a signature brain activity response or a control signal in one or more brain areas during the presentation of a stimulus or a tag flash can indicate that the tag flash is informative for determining the user's intent.

Figure 5C:
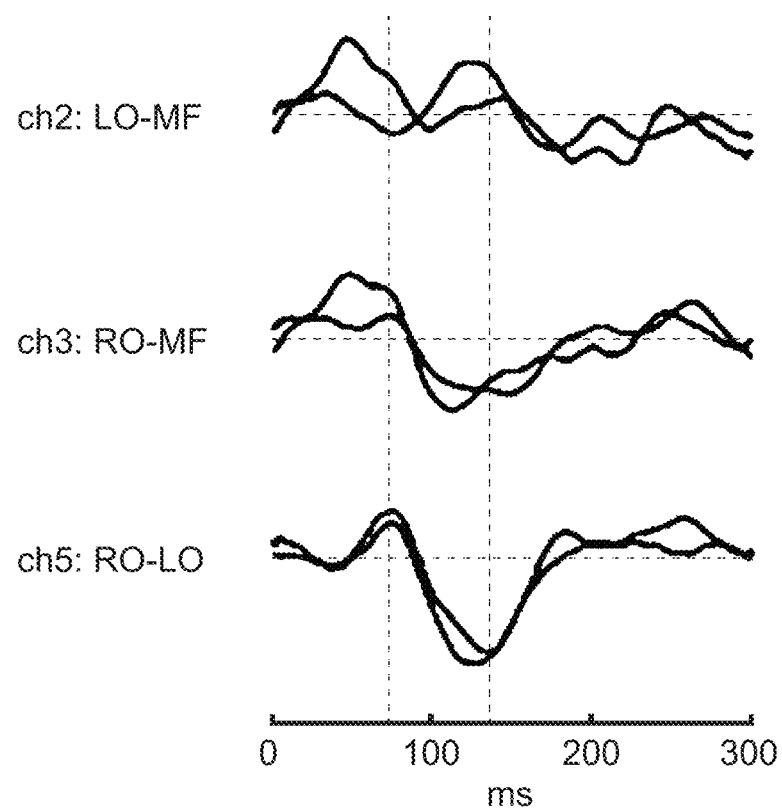
FIG. 5C illustrates example brain signals acquired from various brain regions in response to repeated presentation of a tag-group flash, using a BCI system according to an embodiment.

FIG. 5B illustrates two example neural activity signals that can be acquired during and after the presentation of two stimuli, with stimulus presentation at time point 0. (e.g., presentation of the tag flashes 579A and 579B described in association with FIG. 5A). For example, the signal 573A can be a neural signal evoked and acquired following the tag flash 579A, and the signal 573B acquired following the tag flash 579B, of FIG. 5A, As illustrated, I being the target tag 585, and the target tag 585 being a part of the tag flash 579A, the neural signal 573A in response to the tag flash 579A comprising the target tag 585 can include a signature neural response (e.g., an Event Related Potential or the like) indicated by the transient change in amplitude of the signal shown as a distinct upward deflection of the trace 573A at around the 200-300 ms time point. Based on the method of signal acquisition the control signal can be a change in any suitable parameter. For example, an upward or downward deflection, of a change in frequency, etc. Whereas, signal 573B in response to a tag flash 579B that does not include a target tag 585, can be devoid of any signature neural responses. Neural activity signals can include or not include control signals or signature responses based on the task, stimulus presented and the brain area that the signals are recorded from. FIG. 5C shows example signals recorded from three example brain regions, during the repeated presentation of a stimulus. As shown, stimulus presentation can be repeated one or more times and can help with increasing signal-to-noise ratio and increasing accuracy of determining the target tag. Repetition of stimulus presentation can be used appropriately in consideration with other requirements like speed of user interaction, etc.

Feature Extraction

In some embodiments of the BCE systems 100, 300 or in some embodiments of the process 200 or 400 to implement a BCI system, the signals acquired following stimulus presentation can be used entirely to gather information regarding the user's intent. In some other embodiments of the BCI systems 100,300 or in some embodiments of the process 200 or 400 to implement a BCI system, one or more dimensionality reduction methods can be used to optimally use the information provided by the acquired signal. For example, the analytical procedures used to determine user intent can involve one or more steps of detecting and/or extracting features from the signals acquired, as disclosed above. Features of a signal can include several parameters describing the signal. In some example conditions features can also include components (e.g., Principal or Independent components) of the signal, or values or vectors obtained using other similar dimensionality reduction methods. Some example features can also include peak amplitude, duration, frequency bandwidth, mean deviation from baseline, etc. One or more of the features can be specific to certain other parameters. For example, features can include peak amplitude at 200-500 ms following stimulus presentation, or peak amplitude of frequency response within a specific range of frequencies, etc.

Figure 6A:
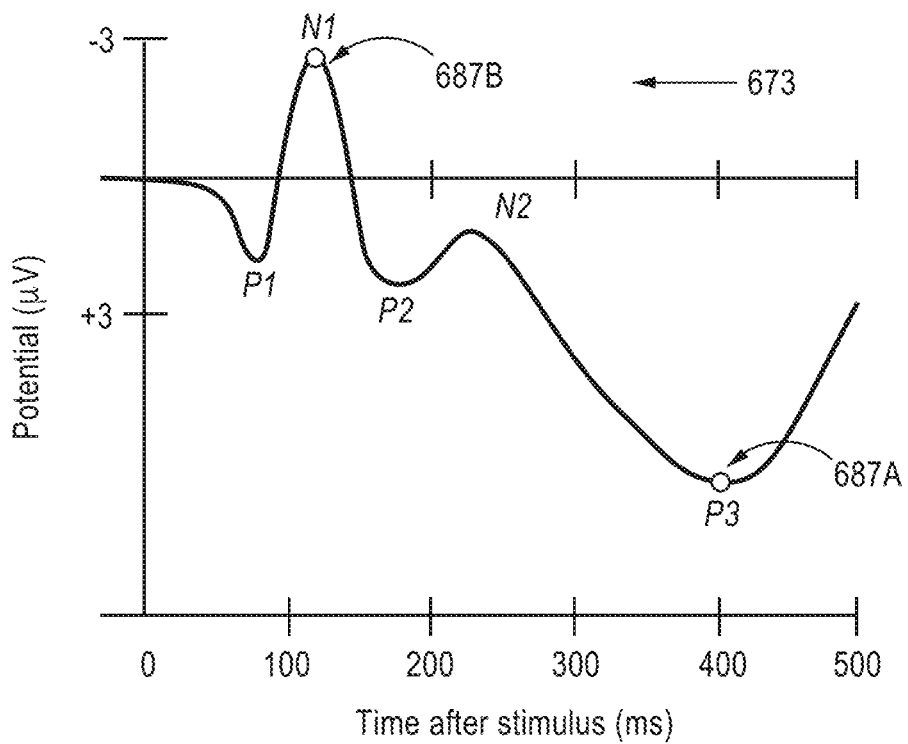
FIG. 6A shows an illustration of a brain activity signal acquired by an embodiment of a BCI system.
Figure 6B:
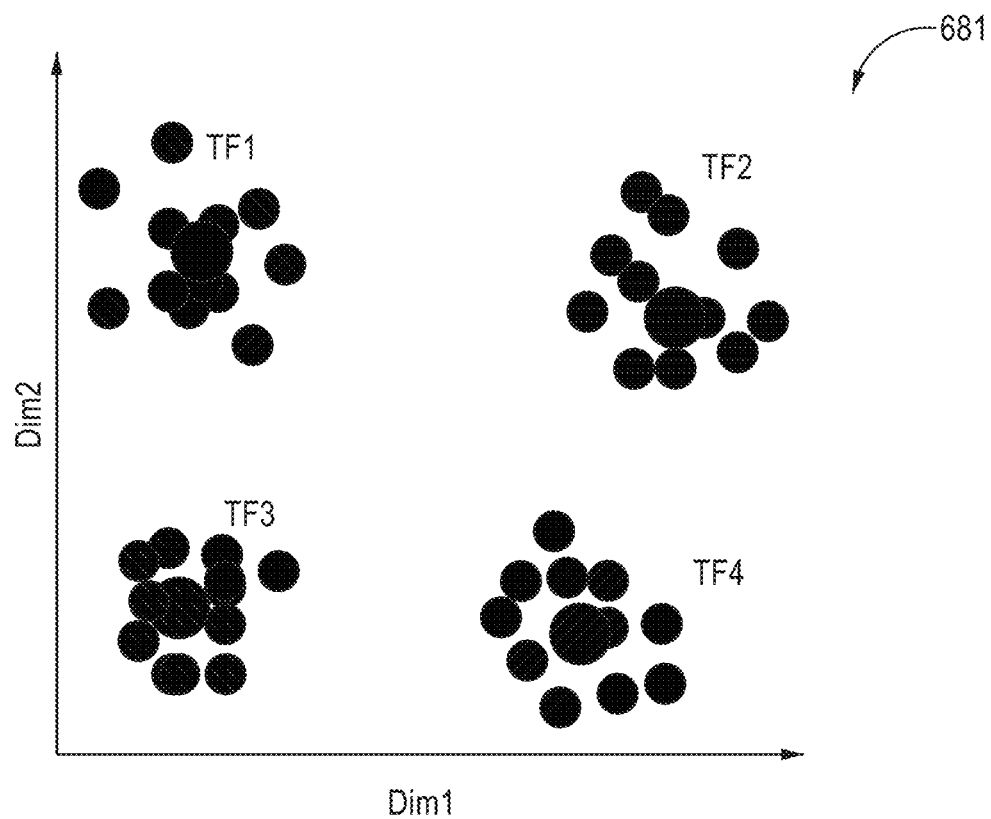
FIG. 6B illustrates an example analysis of brain activity signals by a classifier in a BCI system, according to an embodiment.

An example neural signal is illustrated in FIG. 6A indicating an example feature 687A, the peak amplitude of negative deviation of the neural signal 673 at time point 400 ms after stimulus presentation. Another example feature can be 687B, the peak amplitude of positive deviation at time point between 100 and 200 ms following stimulus presentation. Similarly, one or more features can be defined and used to distinguish between brain activity responses or neural signals evoked by stimuli including a target tag and stimuli not including a target tag. For example, several stimuli or tag flashes can be presented and the concurrent signals can be acquired and the BCI system can run one or more feature extraction routines on the signals acquired to extract one or more particular features, for example, the features 687A and 687B (feature 1 and feature 2) indicated in FIG. 6A. The extracted one or more features from the signals can be considered as dimensions (e.g., Dim 1 and Dim2) and used to evaluate the signals. FIG. 6B illustrates one example way of projecting the extracted features 687A and 687B, as Dim1 and Dim2, extracted from signals acquired during a series of repeated presentations of four stimuli or tag flashes (TF1, TF2, TF3, and TF4). For example, the tag flash TF2 can contain a target tag, registering a larger amplitude on both features 687A and 687B, plotted on axes Dim1 and Dim2, whereas the tag flash TF3 may not include a target tag, registering smaller (or zero) amplitudes for both features 687A and 687B, plotted on each axis Dim1 and Dim2. One or more classifiers or interpreters in the BCI system (e.g., systems 100, 300) or the method to implement a BCI system (e.g., processes 200, 400) can use these features and or dimensions to classify and or label the signals and the stimuli (or tag flashes) evoking the signals, in a suitable manner, as described below.

Identifying a Target Tag

As described above, one of the goals of a BCI system is to present a set of options as stimuli and decode, from neural signals of brain activity, the intent of a user to select one particular stimulus that can mediate a particular action. The set of stimuli can be a set of visible tags of which one particular tag of interest to the user can be a target tag. Thus, said in another way, a goal of a BCI system can be to identify with a certain degree of precision and confidence, the identity of the target tag from the set of available visible tags. The process of identification of the target tag can incorporate several sources of information like the prior likelihood of a specific tag being presented, the likelihood that a specific tag may evoke a signature brain activity response, etc.

Figure 7:
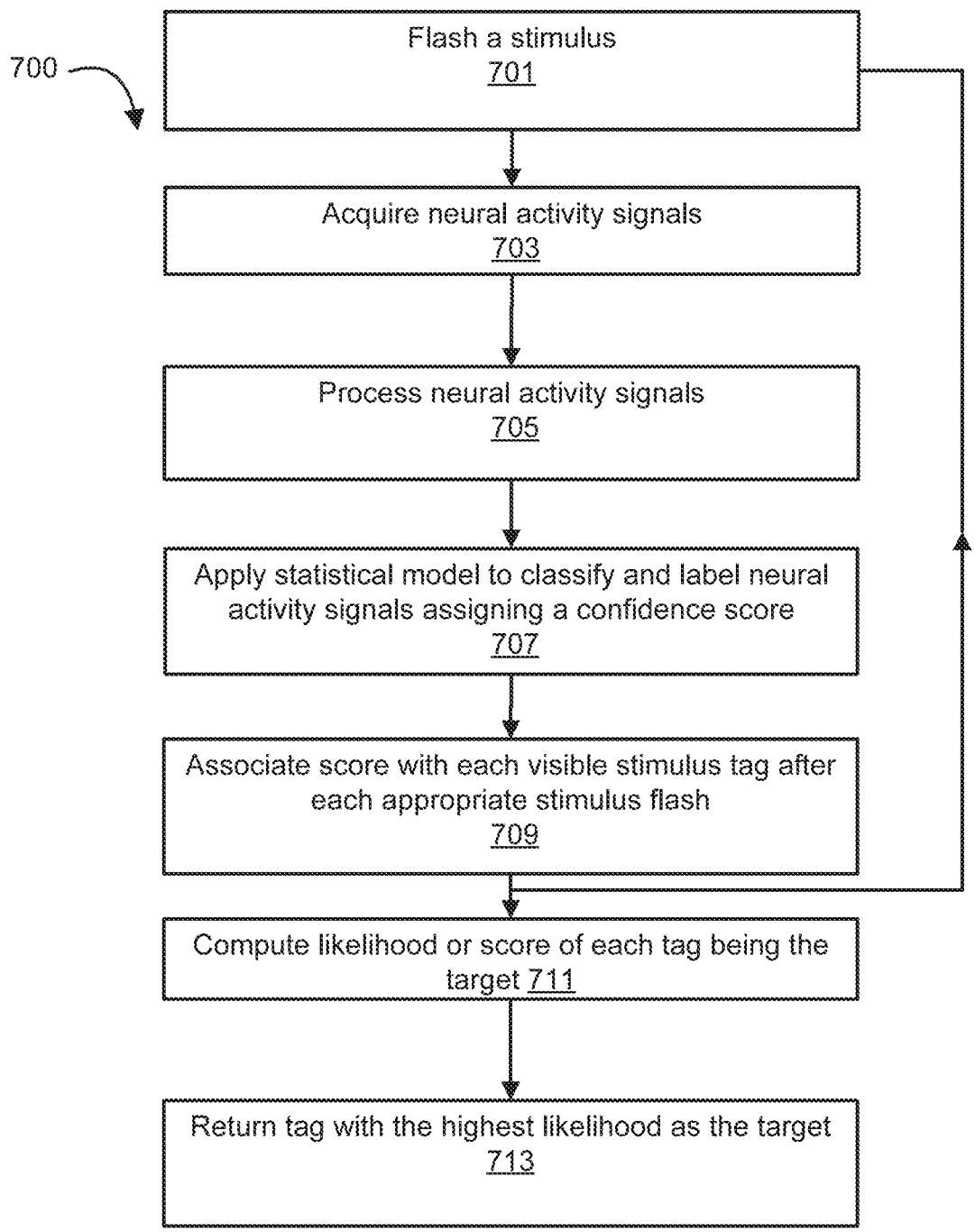
FIG. 7 is a flowchart illustrating an example method of determining the target or tag of interest, in a BCI system, according to an embodiment.

In order to perform this function, a BCI system 100, 300 can implement a process 700 illustrated in FIG. 7. The process 700 can be a portion of or the same or substantially similar to the processes 200 and/or 400 described above. For example, the process 700 can include one or more training and/or a testing sessions, with presentation of training and or new stimuli. The process 700 can also include the acquisition and analysis of signals like neural signals, oculomotor signals, and/or peripheral signals. Accordingly, such similar portions and/or aspects are not described in further detail herein.

As shown in the flowchart in FIG. 7, the process 700 can include a step 701 of stimulus presentation (e.g., a tag or control item flash) and a step 703 of acquisition of the various signals including neural activity signals concurrent and/or following the stimulus presentation of step 701. For example, the process 700 can include presenting, via a control interface, a stimulus. In some embodiments, the processor can be configured to present the stimulus by changing an appearance of the visual representation associated with the stimulus or tag (e.g., control item), such as a size, a color, an orientation, an intensity, a thickness, or a mobility of the visual representation. The process 700, at step 703, can receive, from a neural recording device, a set of neural signals of a user associated with the stimulus after presenting the stimulus. Alternatively or additionally, the process 700 can include receiving, from the eye-tracking device, a set of eye-movement signals associated with the stimulus. At step 705, the acquired signals (e.g., neural signals, eye-movement signals) can be processed appropriately (e.g., pre-processing, filtering, feature extraction, etc.), including processing neural signals to extract information, e.g., associated with a set of features from an EEG signal (e.g., an amplitude of a response included in the neural signal, a duration of the response, a shape of the response, a timing of the response relative to the presentation of a stimulus from the set of stimuli, a frequency associated with the neural signal, etc.), as described above. At step 707, the processed signals can be interpreted by applying any suitable statistical model or mathematical construct to the signals. At step 707 the processed signals can also be classified or labelled or scored based on a confidence scoring system used to compute a likelihood of the signal containing a signature neural response or the likelihood of the neural signal comprising a control signal. At step 709 the processed signal or the labelled/scored signal can be associated with the stimulus or tag flash that evoked the signal. In other words, at step 709 the processed and analyzed results of a neural signal can be associated with or tied to a tag flash causing the response in the signal. The steps 701-709 can be repeated for presentations of various distinct stimuli or tag flashes, or also for the repeated presentation of a single stimulus or tag flash (signals and analytical results from repeated presentations of a stimulus can be averaged to increase signal-to-noise ratio, SNR, provided the conditions are comparable). At step 711 the process 700 can include a determination (e.g., computation) of a likelihood or a score of each visible stimulus or tag (e.g., control item) being the target tag. Following which at step 713, evaluating the likelihoods or scores of all visible tags, the tag with the highest likelihood or score is determined to be the target tag and returned for selection. As described above, the identification of the target tag can also include consideration of the likelihood that a tag may be the target tag, or the likelihood that the tag may be presented. For example, if the UI/UX is a speller of English words, the BCI system can include consideration of the likelihood that a particular letter in the English alphabet may be the target tag, or the probability that a particular letter is presented. This consideration can speed and accuracy of identifying the target tag as some letters are vastly more used in the English language (e.g., vowels) than others (e.g., letters like z, q, etc.). The identification of the target tag can also include and/or be associated with determining a point of focus of the user, Where the point of focus is associated with the stimulus or tag. Based on the tag and/or point of focus, the BCI system can determine an action intended by the user and implement it (e.g., activate or deactivate a tag or control item).

Score Table

A user may be presented with a series or combinations of stimuli or tags via UI/UX of a BCI system like the systems 100, 300. The tags can each be associated with one or more actions that provide the user with control over machines, devices and/or interfaces. At any given step, one (or more) of the tags can be the target tag which when selected can result in the action that the user wants. The goal, as described above, is to identify, from the neural signals (and other associated signal like oculomotor or peripheral signals), the target tag from the assortment of presented tags or tag-groups.

The identification of the target tag can be accomplished using any suitable method of analyzing the neural signals evoked by each presented stimulus or tag (or tag-group). One example method is to calculate, for all possible visible tags, the likelihood that each of the visible tag is the target tag. Each visible tag with a computed likelihood can also be associated with a score according to any suitable scoring scheme. Thus, all visible tags can have a score, forming a score table, which can be evaluated for the highest scoring visible tag to be identified as the target tag, as described in further detail below.

FIG. 8A shows some example analytical methods that can be used to compute the likelihood that a visible tag in a UI/UX of a BCI system is the target tag of interest to a user, in a given instance. The likelihood can be associated with a score, for example a confidence score, that ranks the stimuli or tags presented. For example, a user may be presented with P tags which, when presented as flashes in suitable combinations as tag-groups (t1, t2, etc.), are known to evoke certain target responses and certain non-target responses. The BCE system can generate a feature vector including one or more features, which can be used to score ($y_t$) a stimulus-response evoked during the presentation of a tag (or tag-group) flash, t. The score $y_t$ can be based on a likelihood metric calculated with prior knowledge of responses to known stimuli. For example, the likelihood of a given stimulus response, $x_t$, to a stimulus or a tag flash t, comprising a control signal or a signature response signal (e.g., an ERP or a P300) can be computed by suitable analytical methods, based on whether the tag flash included a target tag, Some example methods are illustrated in FIG. 8A, like 891 and 893. Using the scores of target and non-target tag stimulus-responses distributions can be computed with a mean, ($\mu_a$) and variance ($\sigma_a^2$) for target responses, and a mean ($\mu_n$) and variance ($\sigma_n^2$) for non-target responses, as shown in example distributions illustrated in FIG. 8B.

The probability that a particular tag when presented as a stimulus evoked a signature response can be computed using any suitable method. For example, as illustrated in FIGS. 8A and 8B, the neural signals evoked for each tag presentation can be analyzed, with or without comparison to known signature responses from a training data set, to generate a probability metric using equations such as 891 and 893. The probability metric resulting from the analysis can be used to generate a confidence score 895. The confidence scores corresponding to all the available (visible and invisible) tags, including tags that are presented and tags not presented, can be a distribution of scores. Two example score distributions are illustrated in FIG. 8B. The Null distribution centered around zero score, corresponds to known tags that do not evoke signature responses, which are the non-target tag stimulus-responses with mean ($\mu_n$=0) and variance ($\sigma_n^2$). The sample distribution is of scores arising from potential target tags that may have evoked a signature response, with score mean ($\mu_a$) and variance ($\sigma_a^2$) for the potential target responses. The separation and/or overlap between the distributions may depend on factors related to properties of the stimulus, the user, and/or the UI/UX.

In some embodiments, in order to distinguish whether a particular score (e.g. scores 895 with values 0.3 and 0.9) belongs to the null or the sample distribution, any suitable method may be used. For example, a threshold score value (e.g. score=0.1) can be used as a criterion 897 to aid in allocating whether a tag is a target tag or not. In some other embodiments, the scores from all the tags may not be categorized but compared against each other and the tag with the highest score may be selected as the target tag. In some embodiments, the neural responses may be fed through an ensemble of classifiers developed to suit particular features of the neural responses and the output of the ensemble of classifiers can be used to generate the confidence score, as indicated in example method illustrated in FIG. 9, and described below.

In some embodiments, for example, prior collection and analysis of training data can be used to set meaningful thresholds or criteria, which when met by the acquired signals can denote that a signature response has been evoked. For example, responses evoked by stimuli known to evoke specific signature responses (e.g., P300 responses) can be used to compare responses from unknown or new stimuli. One or more criteria can be set in various parameters for registering signature stimuli. For example, criteria can be set on parameters like amplitude, frequency, brain region, onset latency, duration of response, shape of response, etc. Distributions can be made of one or more of such parameters from known responses evoked by known stimuli that evoke signature or control responses. One or more parameters from new unknown responses evoked by new stimuli can be compared to these distributions to ascertain whether the new responses include one or more signature responses. For example, the amplitude parameter of an example epoch of response to new stimuli can be compared to the distribution, mean and variance of amplitude parameters from known control responses like P300 signals. And based on where the parameter falls in comparison to the distribution, mean and variance of known P300 signals, the response to the new stimulus or tag can be given a confidence score of whether or not it qualifies as a signature or a control brain signal like a P300 signal. Such confidence scores (e.g., P300 scores) can be computed for all new responses to new or unknown stimuli, tabulated, for example, in a Score Table.

The confidence scores computed for each neural response can be associated with the corresponding stimulus or tag that evoked the response. In some embodiments, scores can be computed for each response and responses evoked by the same stimulus (under suitably similar conditions) can be averaged to achieve better signal-noise considerations. In some embodiments, scores of individual stimulus-response pairs can be obtained from parameters being singly compared to prior or expected distributions of parameters. In some embodiments, prior distributions of scores can also be generated to compare computed scores to expected score distributions. By comparing the confidence scores associated with various presented stimuli or tags, tabulated in a Score table, a BCI system can be adapted to find the stimulus or tag that evoked the response with the highest confidence score. Furthermore, tags can be grouped during presentation and the groupings can be varied to allow easy detection of the individual tag within a tag-group that is the target tag that evoked the response with the highest confidence score.

In some embodiments, one or more analytical methods can be used to classify or label signals. The analytical methods can then be evaluated for their merits based on one or more performance parameters. The results of one or more analytical methods can then be combined to generate a score table. For example, neural activity signals can be processed by several classifiers using several statistical models and each processed classification can be evaluated based on accuracy of classification. An ensemble of classifiers can then be selected to be used together to form a combined classification score that is then fed into a Score table.

In some embodiments, a scoring scheme can be adopted based on various other variables. For example, the scoring scheme can be based on the number of visible tags available, the number of known stimuli or tags that evoked a signature response (e.g., known P300 stimuli), the degree of difference between different tags that may evoked a signature response, etc. For example, a scoring scheme can be within a range of values from −1 to +1 through 0, with stimuli or tags that have high likelihood of having evoked a signature response (e.g., P300) having close to +1 and stimuli having the least likelihood of having evoked a signature response having scores close to −1, and intermediate stimuli having ambiguous responses with the scores near 0.

Ensemble of Analytical Methods: Example—Mélange

Figure 9:
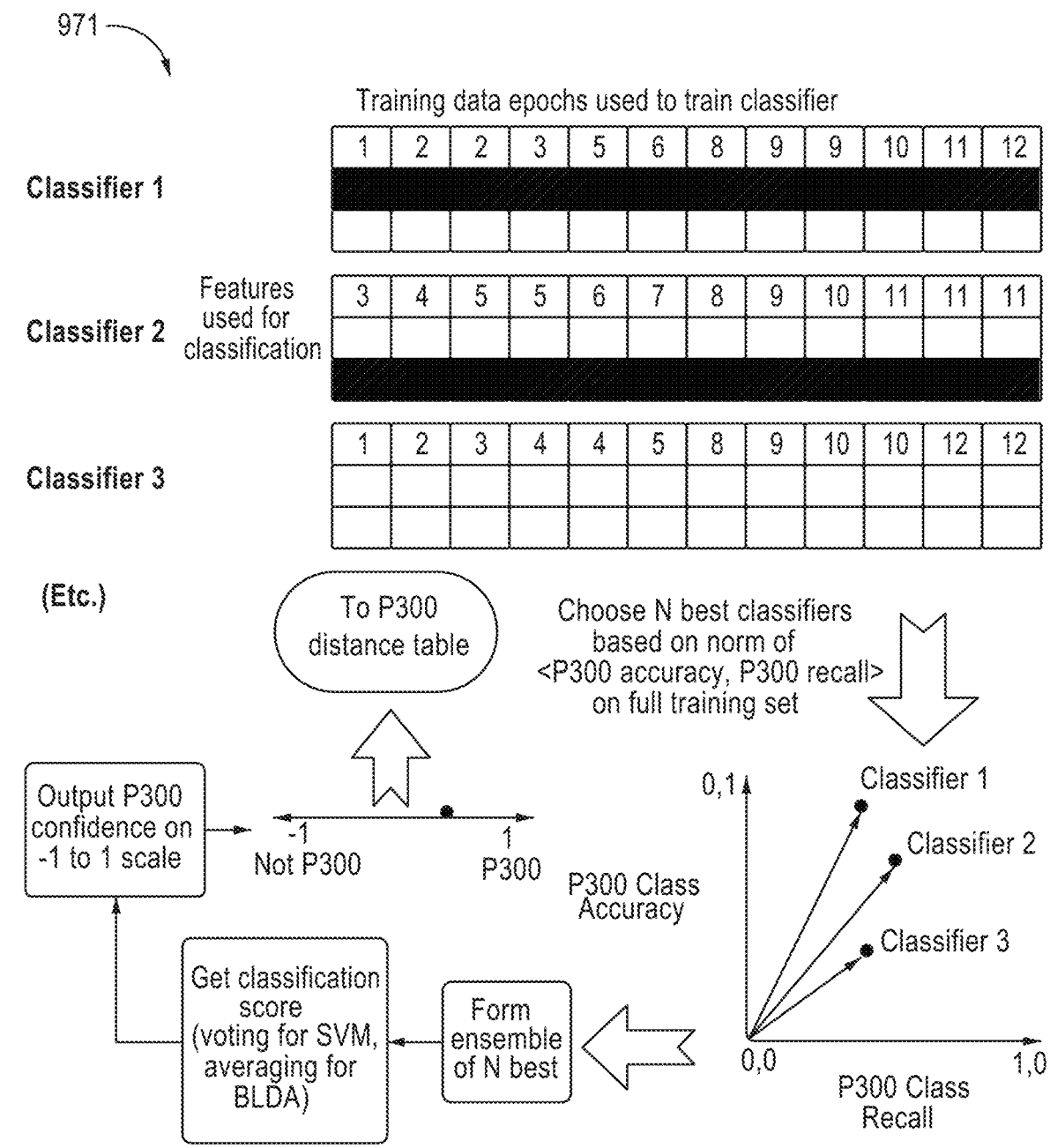
FIG. 9 illustrates a schematic flowchart of an example method of determining a tag of interest, in a BCI system, according to an embodiment.

As described above, in some embodiments, more than one analytical method can be used to generate the score tables, the methods being evaluated based on one or more performance parameters. For example, neural activity signals can be processed by several classifiers with each classifier evaluated against the other classifiers. An ensemble of classifiers can then be used together to form a combined classification score that is then fed into a Score table. The Score table can then be updated with various other sources of information (e.g., stimulus information, information from other signal sources like oculomotor signals, etc.). FIG. 9 illustrates an example method that uses three or more different classifiers that use various feature vectors and classification schemes. The labeling from each of the classifiers is evaluated as shown in the example plot in FIG. 9, The N best classifiers are then selected (N being a predetermined number or user discretion or the like) and an ensemble classifier or the "Melange" is generated. By analyzing the neural signals using the Melange a combined Score Table is generated. This combined Score table can then be updated with other sources of information (e.g., stimulus information, eye-movement information, etc.). For example, the combined Score Table can be fed to be updated by a Distance Table that incorporates proximity based effects of tags on the responses evoked to other nearby tags, described in further detail below, In some embodiments, the classifiers can be configured using score tables (e.g., including one or more score data sets), e.g., during a training phase such as that depicted in FIG. 4. For example, a method can include presenting a stimulus via a control interface to a user, the stimulus including tags (e.g., control items) associated with actions. The method can include receiving, from an eye-tracking device and a neural recording device, a set of inputs associated with behavior of the user. The methods can include generating a score table based on the set of inputs and information associated with the stimulus, and receiving information associated with an action intended by the user (e.g., information indicating the action intended by the user). A set of classifiers can then be configured using the score table and the information associated with the action intended by the user such that the set of classifiers can associate the score table with the action intended by the user, and be later user (e.g., at a later time period) to predict or determine an action intended by the user, e.g., according to method 700 depicted in FIG. 7 or other methods described herein.

In some embodiments, the method can further include modifying, based on evaluating an accuracy of the action determined using the set of classifiers, the set of classifiers to generate a modified set of classifiers. Additionally or alternatively, the method can include generating, based on evaluating the accuracy of the action that is determined, a set of weights applied to inputs received from one or more of the eye-tracking device or the neural recording device. The weights can be associated with the accuracy of the action that is determined, an experience of the user, and historical information associated with the user. The method then includes presenting, at a later time period, the stimulus via the control interface to the user, and receiving, from the eye-tracking device and the neural recording device, a set of inputs associated with behavior of the user at the later time period. The method can include generating a score table or score data set based on the set of inputs and information associated with the stimulus presented at the later time period, and optionally applying the set of weights to the scores in the score table. The method can also include determining, using the modified set of classifiers, an action intended by the user at the later time period.

Using Stimulus Information: Example—Distance Scaling

In some embodiments, of the BCI systems 100, 300 and/or the processes, 200, 400, and/or 700, of implementing a BCI system, the information available about the manner in which the stimuli were presented can be used to improve the accuracy of identification of the target tag. For example, the spatial positioning of stimuli or tag flashes presented through the UI/UX, the temporal order or sequence of the tag flashes, the grouping of tags in a tag-group, degree of salience associated with a tag flash, etc. can be used in conjunction with the likelihood and confidence scores computed from the neural signals as described above with reference to the process 700.

One example method of using stimulus information is described herein, in the form of Distance Scaling to generate what are referred to as Distance Tables. For example, in some embodiments of a BCI system presenting a UI/UX though a visual interface, the physical distance between tags presented as stimuli can be used to better estimate the likelihood that any particular tag is the target tag. In other words, the Euclidean distance between the presented tags in a display can be used to update the confidence scores, in the Score table, computed for each visible tag on the basis of analysis of the response(s) evoked by that stimulus.

Figure 10A:
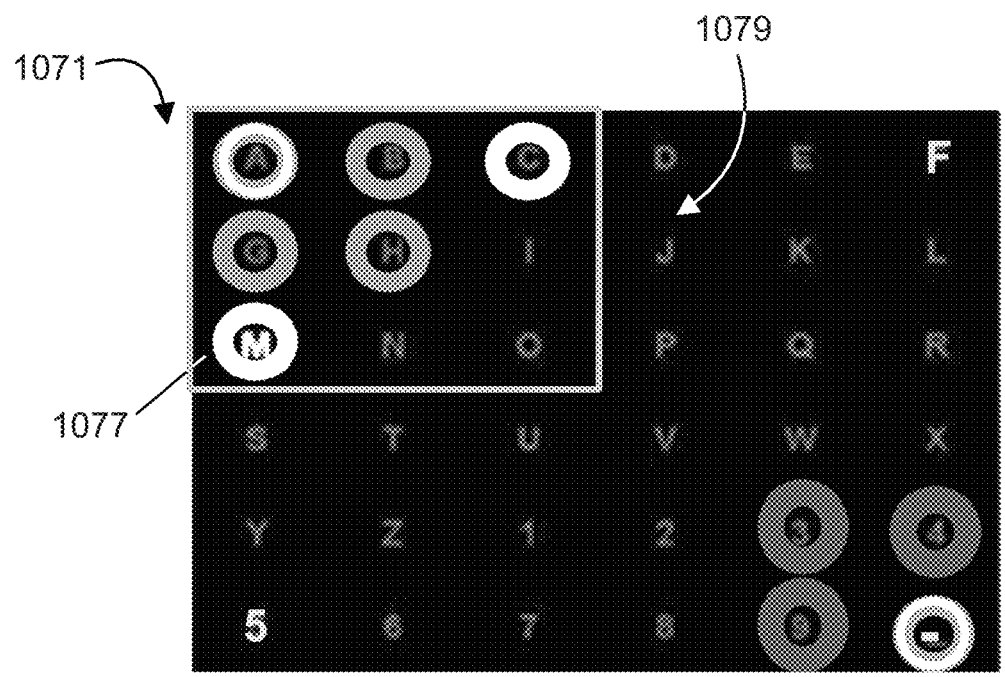
FIG. 10A shows an example UI/UX with visible tags or symbols, illustrating the distance dependent relationship between tags used to determine the tag of interest, according to an embodiment.
Figure 10B:
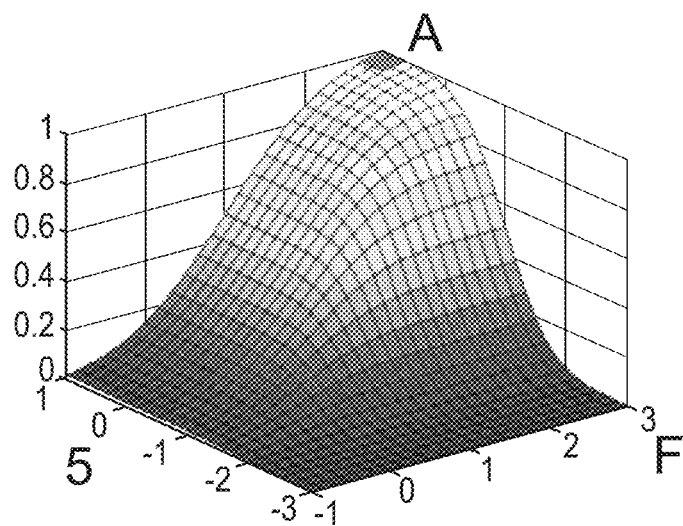
FIGS. 10B and 10C illustrate the distance dependent relationship between brain signal activities evoked by nearby tags, used to determine the target tag, according to an embodiment.
Figure 10C:
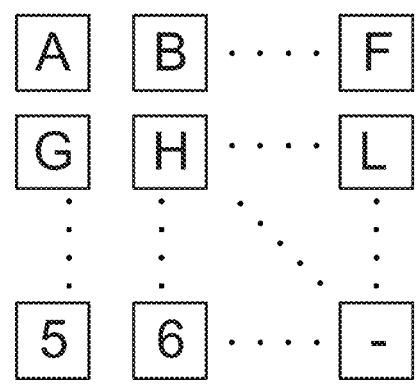

When a particular tag is the target tag (e.g., the letter A shown in FIG. 10A), that target tag A), when presented singly or in tag-groups (e.g., presentation of column or row containing A) can evoke a signature response or a control signal that can be recorded in the neural activity signal. Following the steps of computing a likelihood and/or a score associated with all tags, this particular tag (A) can be associated with in a high confidence score in the Score Table (indicated by the red colored circle). Notably in some embodiments, even when the target tag (e.g., A) is not presented, the presentation of tags that are nearby this target tag (e.g., letters B, G, H, M, C that are in spatial proximity to A) can also evoke a neural response that can be similar to a control signal, resulting in a high score. In other words, some visible tags that are not the target tag of interest can, when presented, also evoke signals similar to a control signal generating a high confidence score, by virtue of their proximity to the target tag. FIG. 10B shows an example plot of signal amplitudes evoked by the presentation of tags shown in FIG. 10C, due to their proximity to the target tag A.

While signals evoked by tags proximal to a target tag can be not quite as salient as the signals evoked by the target tag, they can nevertheless be significant to meet certain criteria or cross-certain thresholds of analyses. However, these signals from proximal tags can be taken advantage of, during the process of identifying the target tag, for disambiguating and/or distinguishing the target tag from tags that may have comparably high confidence scores in the Score Table due to various reasons like temporal proximity, distraction, random spurious signals, etc.

Figure 11:
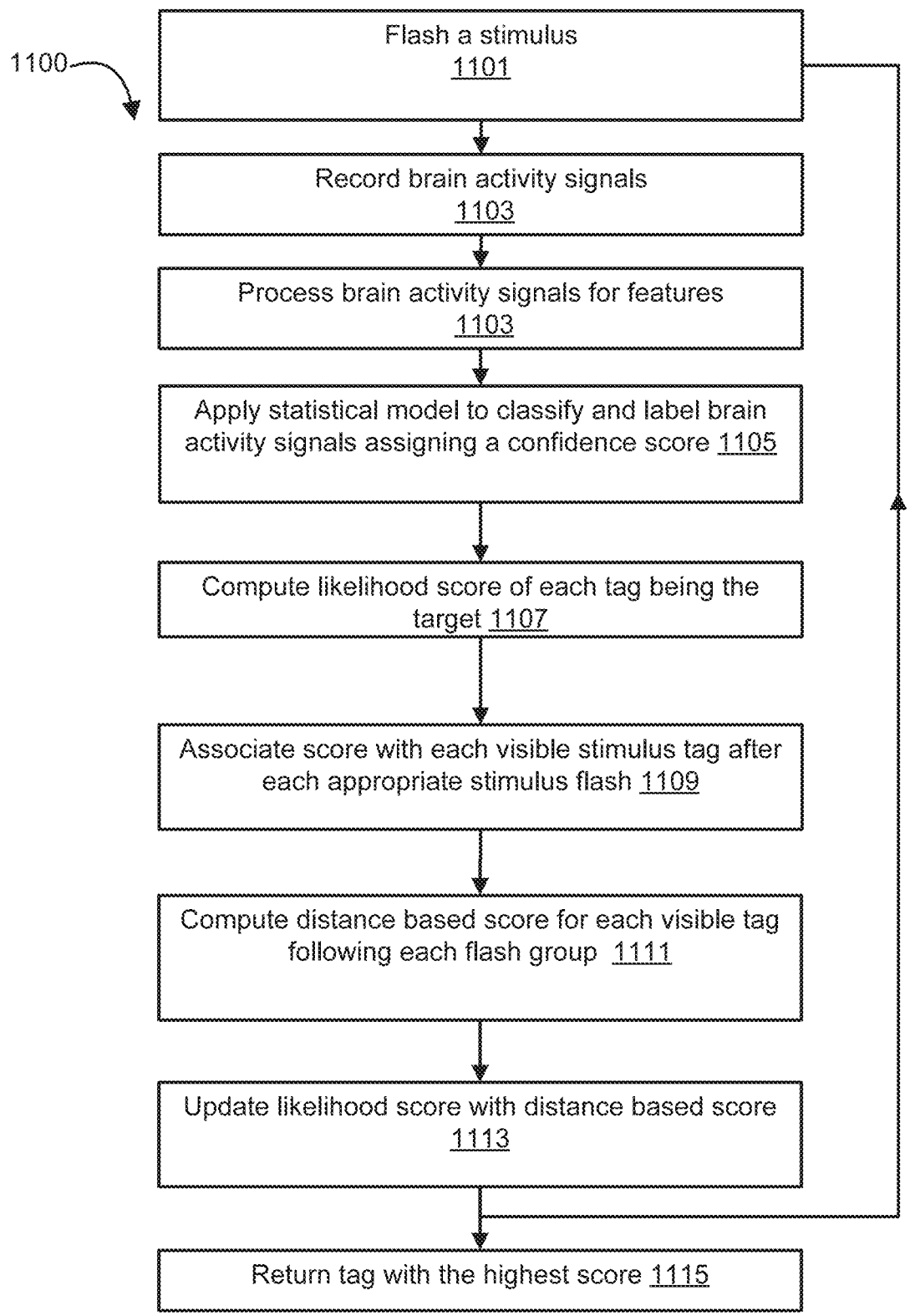
FIG. 11 is a flowchart illustrating an example method determining the target or tag of interest, in a BCI system, according to an embodiment.

For example, in some instance when two tags, like the letter A, and the symbol -, when presented together in a tag flash or when presented or in close temporal sequence, can evoke a signal with a signature response, e.g., a P300 and generate a high score. An example BCI system can use information about the spatial positioning of alt the visible tags in conjunction with stimulus-response information from previously presented tags to correctly identify the target tag to be the letter A. For example, the BCI system can compare responses to presentations of various tags including letters proximal to A (e.g. letters B, G, H) which may have generated high scores (indicated by circles around letters B, G, and H) due to their proximity to A, and letters distal to A but proximal to the high scoring character "-" (e.g., numbers 3, 4, 9), with lower scores (indicated by circles around numbers 3, 4, and 9) due to their distance from the target tag A, to correctly identify that the target tag is A, and not the character "-". While the example in FIG. 10A illustrates how spatial relationship of tags can be used to account for and/or disambiguate comparable scores from two or more tags, similarly, temporal relationship of tags when presented can also be used to account for and/or disambiguate tags with comparable responses. FIG. 11 illustrates an example process 1100 that uses the signals evoked by proximal tags to update the scores in a score table.

The process 1100 can be the same or similar to the process 700 illustrated in FIG. 7. For example, the process 1100 can include a step 1101 of presenting a stimulus or a tag flash with one or more tags, a step 1103 of recording brain activity signals. Process 1100 can also include one or more steps 1103, 1105, and 1107, of processing the brain activity signals, classifying and/or scoring the signals, computing likelihoods. The process 1100 can also include a step 1109 of associating each visible tag with a score and generating a score table. In addition, the process 1100 can include a step 1111 of computing one or more distance scores for each visible score after each tag flash, based on the proximity of that visible tag to the one or more tags that were flashed in a particular instance of stimulus or tag flash.

In other words, following each tag flash, the step 1111 includes computing a score for each of all the tags available (e.g., a distance score) based on the proximity of that tag to each of the flashed tags, generating a Distance Table. The distance scores from the Distance Table can be used to update the confidence score in the Score Table, at step 1113. Following which, at step 1115, the updated Score Table can be evaluated for the tag associated with the highest score, and that tag can be determined to by the target tag.

Figure 12:
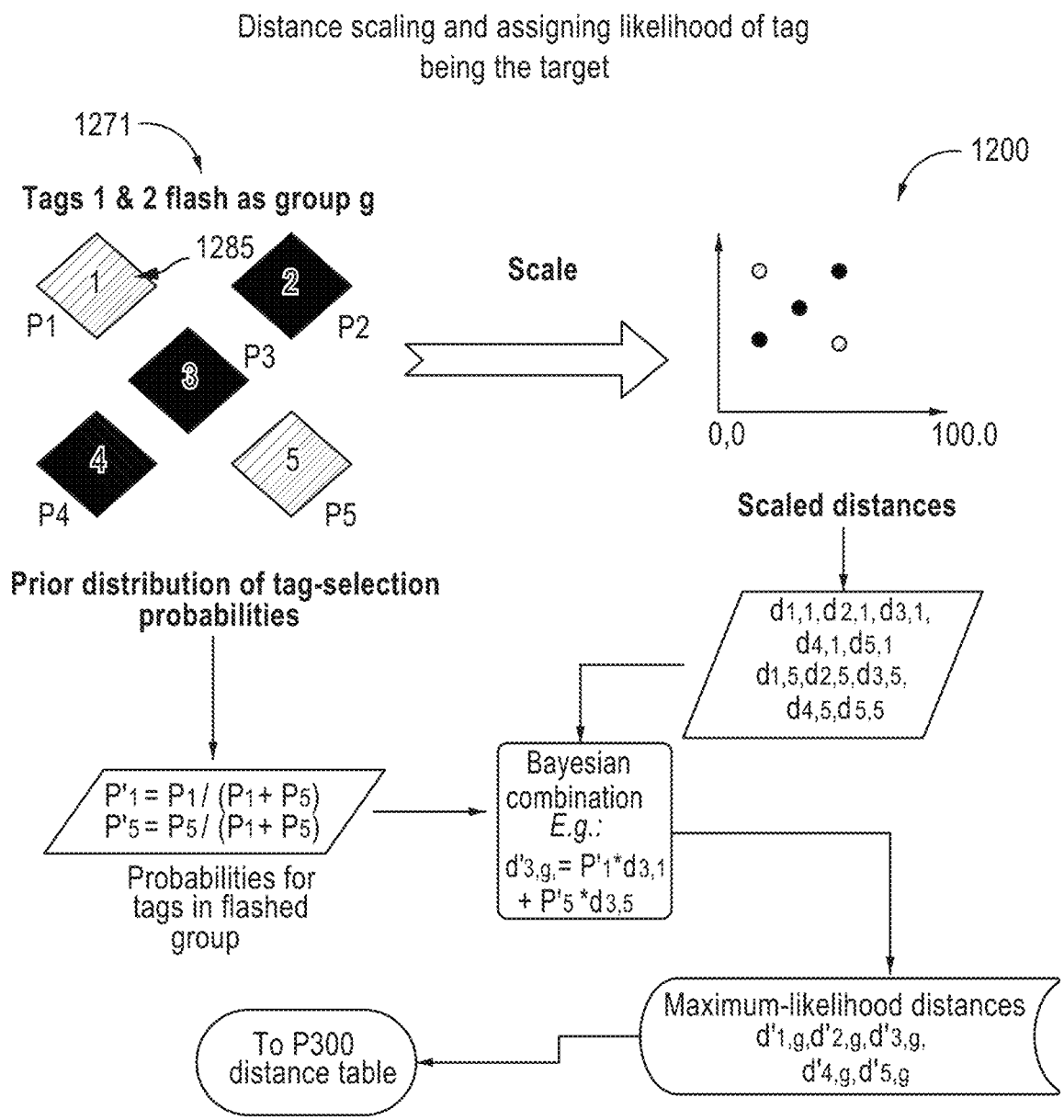
FIG. 12 illustrates a schematic flowchart of an example method of distance based scaling of scores associated with tags in determining a tag of interest, according to an embodiment.

FIG. 12 illustrates an example method of calculating distance scores to generate the distance table. For example, tags 1-5 can be a set of available tags of which a user wants to select tag 1. Thus tag 1 is the target tag. At a given instance of the UI/UX, tags 1 and 5 can be presented together as a grouped tag flash. Each tag in the set of available tags can have a prior probability of being presented. For example, if there are 5 tags and all are equally likely to be presented, then each of the five tags can have a presentation probability of ⅕ (0.2). Similarly, two or more tags in the set of available tags can have a prior probability of being selected together. For example, the tags 1 and 5, flashed together in the tag-group (1, 5), can each have a prior probability of being presented given by their individual probabilities normalized by the sum of their probabilities, as indicated in FIG. 12.

Distance measures can be computed for each of the tags from every other tag as shown in FIG. 12. For example, the distance from the tag 1 to every other available tag 1-5 can be computed as the measures $d_{i1}$ (i=1, 2, 3, 4, 5). Following the calculation of prior probabilities and distance measures, each visible tag (1, 2, 3, 4, 5) can be assigned a likelihood measure of that tag being the target, scaled by the distance measure from each tag flash. That is, each visible tag can be assigned a prior likelihood score of being the target tag regardless of which tag is being flashed, and then with each tag flash, the likelihood score of each visible tag can be updated with appropriate distance scaling from the tags in the latest tag flash or tag-group flash. For example, when the tag-group (consisting of tags 1 and 5) is flashed, the likelihood that a tag x (e.g., tag 3) is the target tag can be scored to be $d'_{x,g}$ (e.g., $d'_{3,g}$) Given by the sum of the presentation probabilities (p'1 and p'5), of the tags in the flashed group (1 and 5), each presentation probability (p' 1 or p'5) scaled by the corresponding distance ($d_{3,1}$ or $d_{3,5}$) of that tag (1 or 5) from the scored tag (3). As illustrated in the example in FIG. 12, all visible tags can thus be assigned a distance based likelihood score or a Distance score, from information about the presentation of each tag. The collection of all distance scores in a Distance Table (e.g., P300 Distance Table) which can then be fed to update a Score Table (e.g., P300 score table) that is generated from analysis of neural activity signals and computation of confidence scores, as described above.

Figure 13:
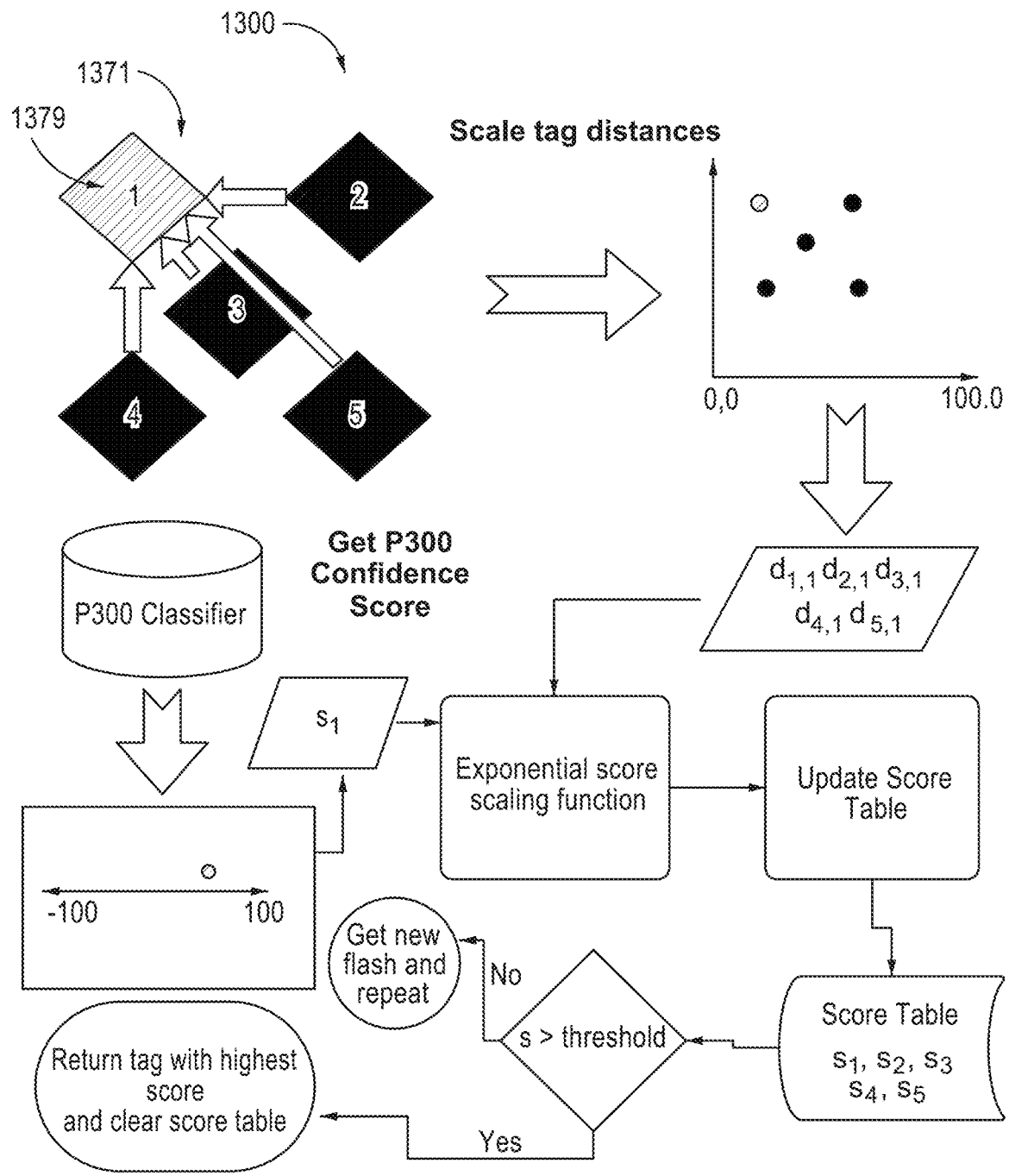
FIG. 13 illustrates a schematic flowchart of an example method of incorporating distance based scaling of scores in determining a tag of interest, according to an embodiment.

FIG. 13 illustrates another example sequence of step followed by a process similar to process 1110 wherein the confidence scores of a Score table from analyzing the neural activity signals (e.g., using a classifier) and distance scores from a distance table can be combined to form an updated Score table with scores s1, s2, s3, etc., which can then be evaluated to identify the tag or stimulus with the highest score as the target tag. As shown in FIG. 13, generating a Score table with confidence scores, updating the Score Table with Distance scores and evaluating the updated Score table can be carried out after each stimulus or tag flash. If a distinct stimulus of tag can be identified as the target tag on the basis of having the highest score, as well as the highest score meeting one or more threshold criteria, the identified target tag can be returned to be selected, terminating that instance of target tag identification and clearing the Score table.

However, when no tag (including the tag with the highest score in the Score table) has a score meets the one or more threshold criteria, and thus no tag can be identified as the target tag, this result can indicate a state of insufficient data which might lead to the UI/UX proceeding to another sequence of a new tag flash followed by computation of confidence scores, computation of distance scores and updating of the Score table to incorporate data from the latest tag flash. The updated Score table can then be evaluated again for the highest score to meet the threshold criteria. This sequence of a new tag flash followed by computation of confidence scores and distance scores to update the Score table can continue repeatedly until the Score table reaches a state where at least on tag has a score that meets the threshold criterion for being identified as the target tag.

Using Eye-movement Signals: Example—Visual Score Table

In some embodiment of a BCI system (e.g., systems 100, 300) or a process to implement a BCI system (e.g., processes 200, 400, 700, 1100, and/or 1400) can be configured to incorporate eye-movement information available from one or more eye-trackers. That is information from one or more oculomotor signals can be used to update a Score table to identify the target tag from a set of available tags.

Figure 14:
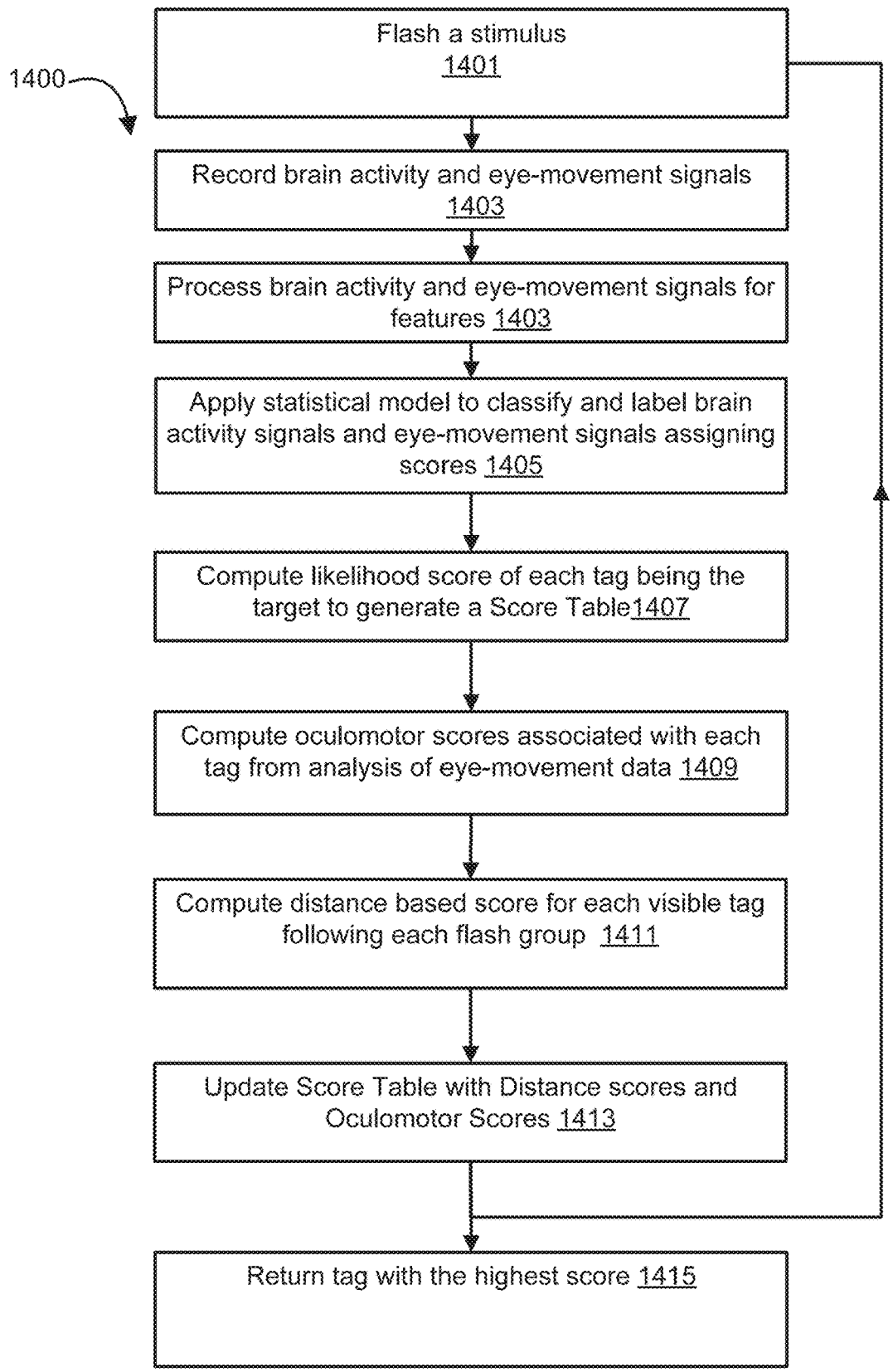
FIG. 14 is a flowchart illustrating an example method of determining the target or tag of interest, in a BCI system, according to an embodiment.

FIG. 14 shows a flowchart outlining a process 1400. The process 1400 can be the same or substantially similar to processes 200, 400, 700, and/or 1100. For example, the process 1400 can include a step 1401 of presenting a stimulus or a tag flash with one or more tags. The process 1400 can include a step 1403 of recording brain activity signals and eye-movement signals. At steps 1405, and 1407, the acquired brain activity signals and eye-movement signals can be processed and suitable statistical models may be applied, respectively. Following which scores can be assigned or associated with tags based on analysis of brain activity signals using one or more suitable scoring schemes. At step 1407 a likelihood metric can be calculated, for each tag being the target tag, based on the one or more scores.

Figure 15:
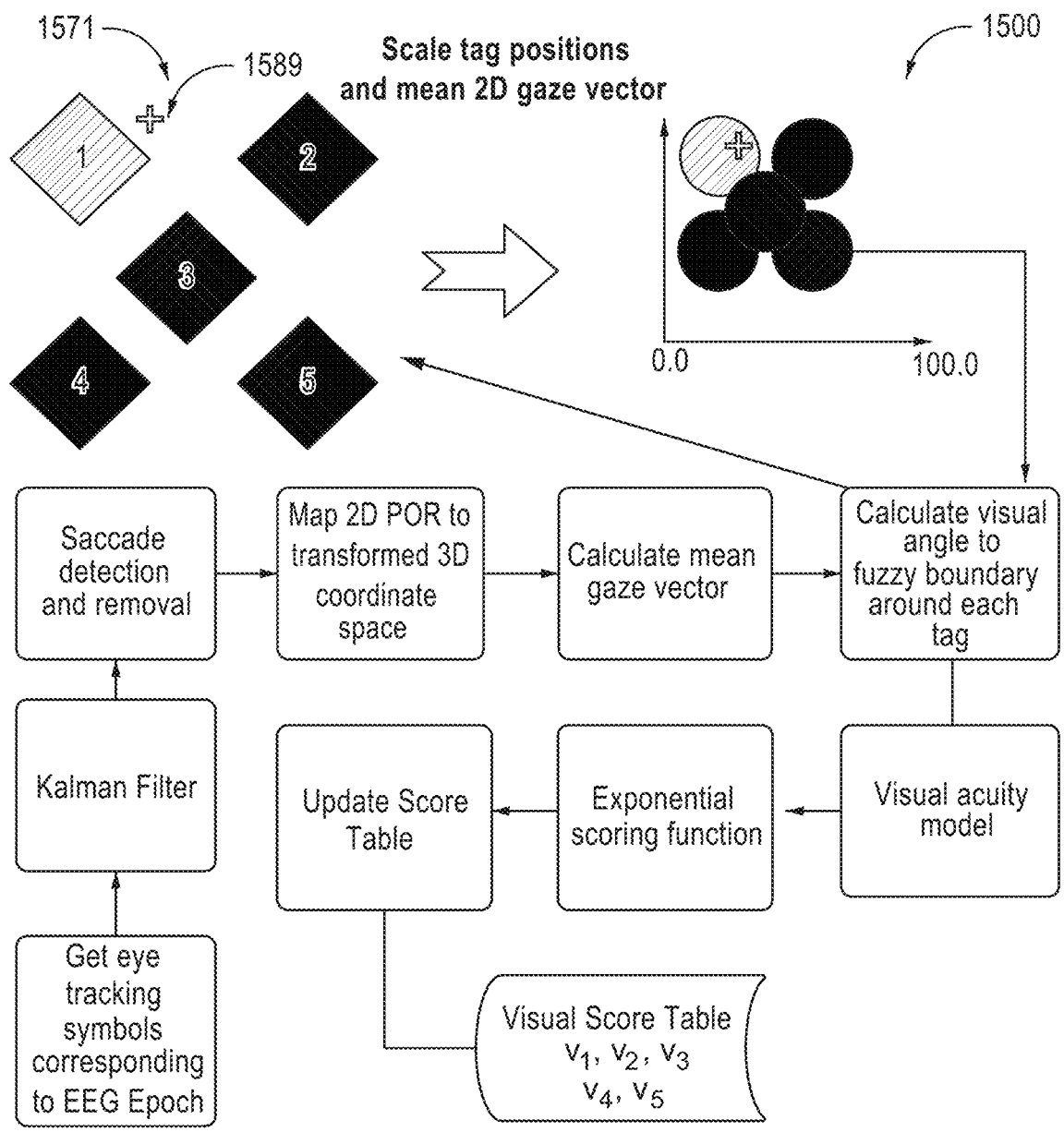
FIG. 15 illustrates a schematic flowchart of an example procedure of generating a visual score based on eye-movement signals, according to an embodiment.

In addition, the process 1400 can include a step 1409 to compute oculomotor scores associated with each tag. Following computation in steps 1409 and 1411, the Score table of step 1407 can be updated with the Distance scores from a Distance table and/or Oculomotor scores from a Visual Score table. The updated Score table can then be evaluated in step 1415 to identify the target tag. The Vision table can be generated by computing oculomotor scores using any suitable method to incorporate eye-movement information acquired concurrent with stimulus presentation and acquisition of neural activity signals. FIG. 15 illustrates and example procedure used in some embodiments, to compute oculomotor scores to generate the Visual Score table.

As shown in FIG. 15, eye-tracking signals acquired corresponding to the acquisition of neural activity signals (e.g., EEG signals) can be pre-processed using any suitable analytical method. For example, the eye-tracking signals can be filtered (using for example a Kalman filtering approach) and can be run through a saccade detection and/or removal routine. Following which, in some embodiments using three dimensional UI/UX, the eye-movement signals corresponding to detected saccades can be transformed from being mapped to two-dimensional space to being mapped on to three dimensional space. In some embodiments, the eye-tracking signals can be acquired and analyzed using apparatus and/or methods that are substantially similar or the same as those described in the '253 application, the disclosure of which is incorporated herein by reference in its entirety above, and/or those described in the '209 application, the disclosure of which is incorporated herein by reference in its entirety above.

In some embodiments, where the UI/UX is designed to be two dimensional in nature, the eye-movement signals corresponding to saccades is retained in two dimensional mapping.

Following mapping, one or more gaze vectors can be computed to generate a magnitude and direction estimate of a user's gaze. The gaze vector computed can have a mean estimate of amplitude and direction as well as variance of gaze angle. A BCI system or a process implementing a BCI system can include computation of a fuzzy boundary of gaze angles or visual angles around each visible tag of the given set of available tags using which a user may view the tag. The BCI system can build and/or update a visual acuity model, using eye-movement kinematics and information about eye-movements of users to generate a predicted gaze vector 189 illustrated in FIG. 15, using the UI/UX 1571. The BCI system 1500 in the example in FIG. 15 can incorporate expected visual angles from the acuity model, in conjunction with other user data available (e.g., eye spacing of a user, make and model of an eye-tracker, etc.). Using the combination of results from the acuity model and the saccadic eye-movement signals and gaze vectors analyzed, a Visual Score table can be generated with oculomotor scores assigned to each visible tag based on its proximity to the calculated gaze vector 1589 As shown in FIG. 15, the Visual Score table with scores v1, v2, v3, etc. can be used to update the Score table computed from confidence scores (and/or updated with distance scores)

Using Sensory Information to Update Score Table

In some embodiment of a BCI system (e.g., systems 100, 300) or a process to implement a BCI system (e.g., processes 200, 400, 700, 1100, 1400, and/or 1600) can be configured to incorporate information available from any number of sensors acquiring biological (or non-biological) data. For example, information from one or more physiological signals, or behavioral signals, or external signals (indicating perturbations or events in the immediate environment of a user, etc.) can be used to update a Combined Score table to identify the target tag from a set of available tags.

Figure 16:
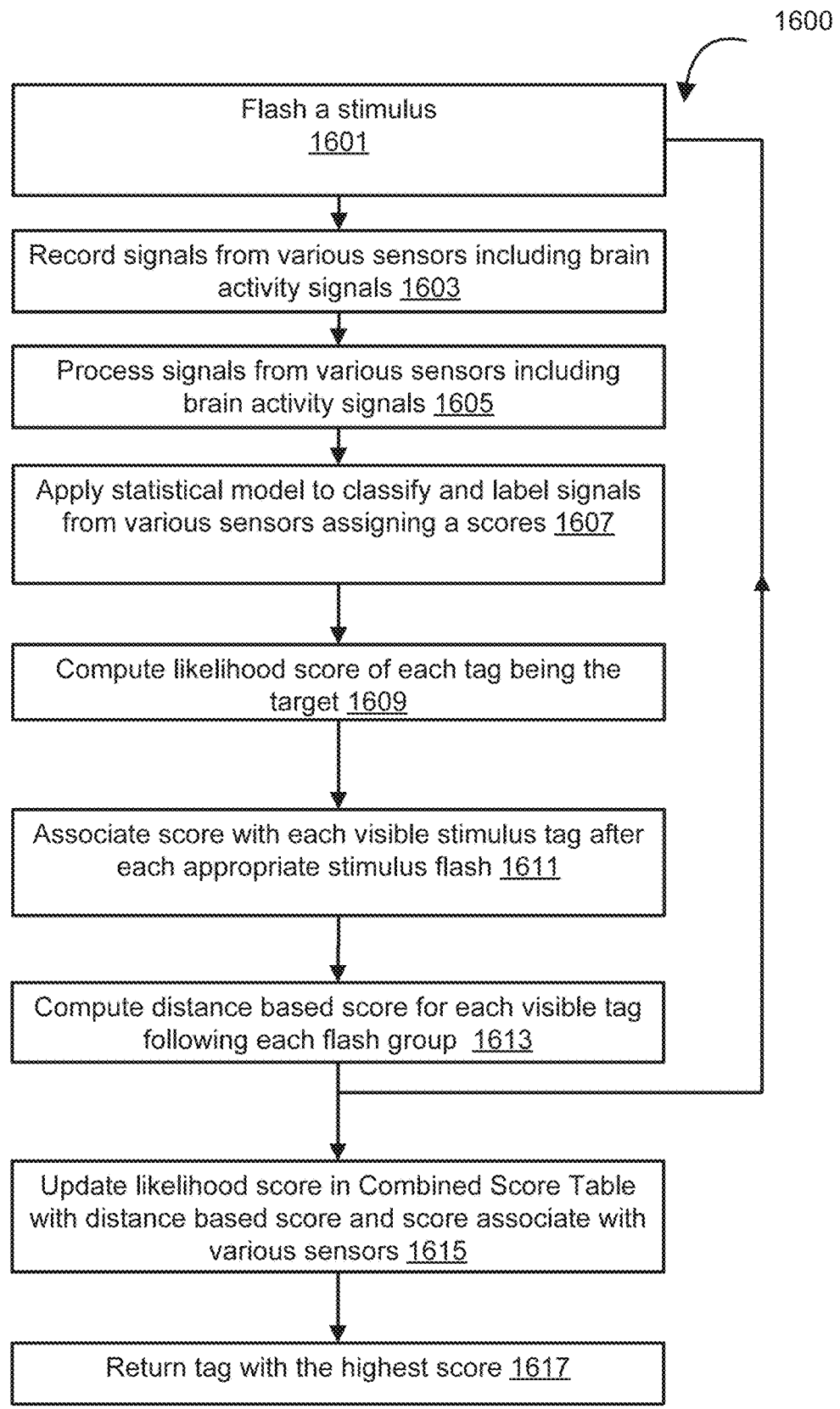
FIG. 16 is a flowchart illustrating an example method of determining the target tag of interest incorporating signals from various sensors, according to an embodiment.

FIG. 16 shows a flowchart outlining an example process 1600 that integrates data from various sensors to form a Combined Score Table. The process 1600 can be the same or substantially similar to processes 200, 400, 700, 1100, and/or 1400. For example, the process 1600 can include a step 1601 of presenting a stimulus or a tag flash with one or more tags. The process 1600 can include a step 1603 of recording brain activity signals and concurrent signals from an array of various sensors. At steps 1605, and 1607, the acquired brain activity signals and signals from various sensors can be processed and suitable statistical models may be applied, separately or jointly as an ensemble, with suitable weighting vectors for each signal stream. Likelihood scores can be calculated at step 1609 and assigned or associated with tags at step 1611, based on analysis of brain activity signals and by analysis of signals from each of the various sensors, using one or more suitable scoring schemes. That is, for every tag flash, in addition to scores for tags from analysis of brain activity signals updating a Main Score Table, every stream of signal from each of the sensors (1, 2, . . . X) can be associated with a score (S1, S2, . . . SX) updated into a Sensor (1, 2 . . . X)—Score Table, for example. The process 1600 may include a step 1613 of updating the Main Score Table with the scores from the Score Tables corresponding to each of the sensors (1, 2 . . . X), generating a Combined Score Table. At step 1617, the process 1600 can return a tag with the highest score in the Combined Score Table as the target tag.

Using a Master Score Table

Figure 17:
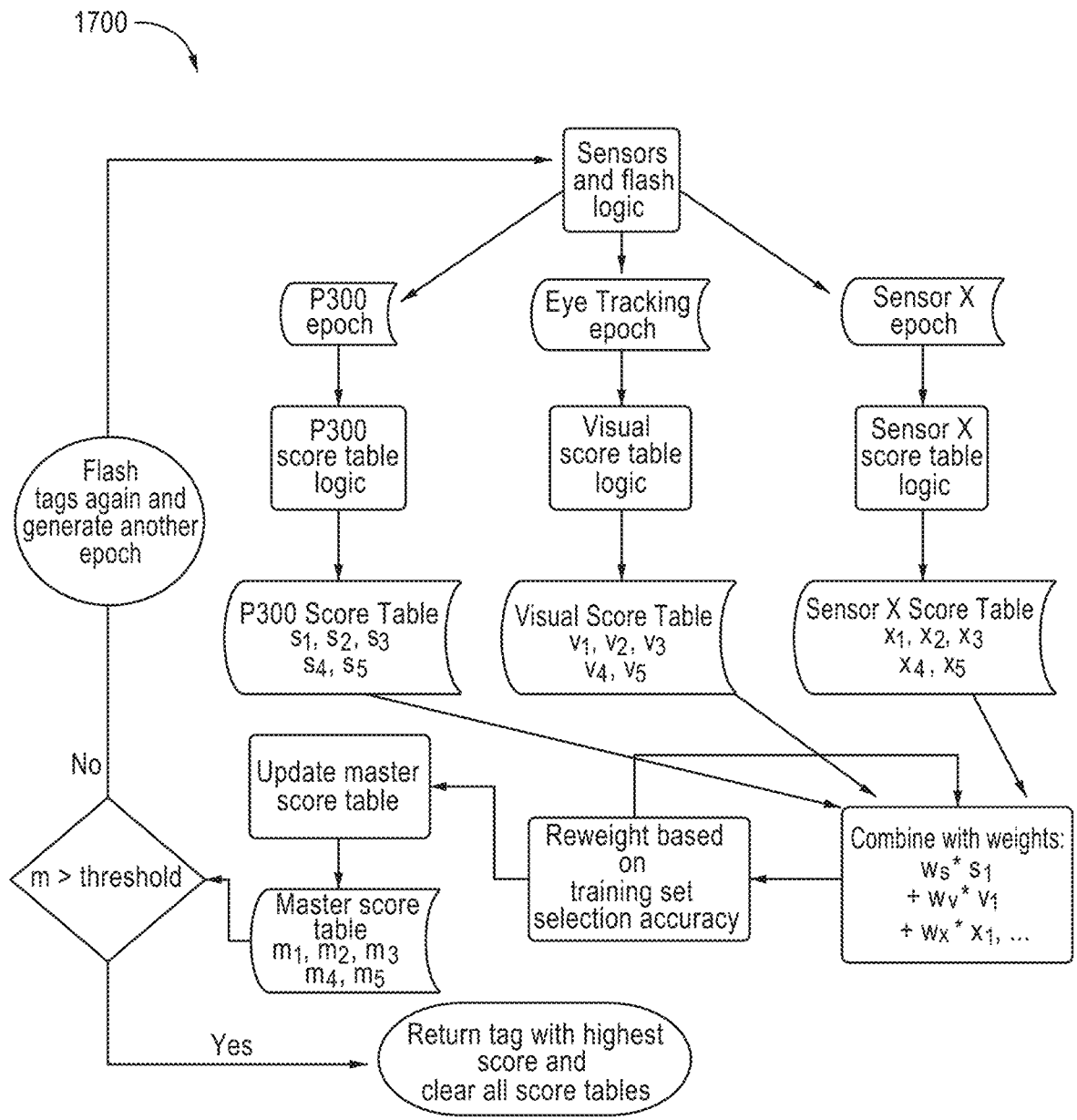
FIG. 17 illustrates a flowchart of an example procedure of combining analysis of signals from various sensors to determine a target tag, according to an embodiment.

FIG. 17 shows an example method 1700 of generating a Master Score table incorporating several source of information to aid in identifying a target tag. For example, as indicated in FIG. 17, the several sources of information can each be used to generate sets of scores and the various sets of scores can be combined suitable to update the identification of the target tag.

In some embodiments, the various scores from various sources of information can be further analyzed by feeding through an ensemble of classifiers. The various scores can be, for example, Confidence scores from analysis of neural responses (e.g. P300 scores as indicated in FIG. 17), Distance scores generated from using information about spatial relationships between tags, Temporal scores from using information about temporal sequence of tag presentation, Vision scores using information about position of the user's eyes and/or head (e.g. from analysis of epochs of eye movement tracking or head movement tracking data), other sensory scores using information about other sensory parameters obtained from sensors (e.g. Sensor X) worn by the user or placed in the user's environment (e.g. voice commands, head movements, gestures, etc.). As indicated in the method 1700 illustrated in FIG. 17, one or more of these scores corresponding to each available tag, from their respective score tables, can be combined to form an ensemble score data set.

In some embodiments, the scores from the score tables can be fed through an ensemble of classifiers such as the example ensemble classifier illustrated in FIG. 9. The ensemble of classifiers can then be used together to form a combined classification score that is then fed into a Master Score table. As illustrated in FIG. 9, for example, Confidence scores may be best classified by classifier I while Distance scores may be best classified by classifier 2, and so on, with each set of scores having a corresponding set of N best classifiers. The N best classifiers are then selected (N being a predetermined number or user discretion or the like) and an ensemble classifier (e.g. the "Melange") is generated. The combined ensemble classifier, (e.g. the Melange) can appropriately use the N best classifiers for the particular data set containing scores from each score table corresponding to each source of information. In some embodiments, the combined scores can be weighted based on their classification.

In some embodiments of BCI systems using a method similar to method 1700, the weighting of scores from several score tables (with or without using an ensemble classifier) can be based on how informative each source of information may be. In some embodiments, as indicated in FIG. 17, the combined weighted set of scores (with or without ensemble classification) can be reweighted, in some instances, according parameters like training set selection accuracy, performance of user during training etc. In some embodiments, the combined set of scores can also be appropriately weighted according to suitable sources of information like user history, level of experience, UI/UX history, user statistics, etc. The resultant combined weighted set of scores for all the visible tags can be used to generate a Master Score Table as shown in FIG. 17. This Master Score table can then be evaluated using a suitable approach such as a threshold crossing criterion, to identify the tag with the highest score as the target tag, Multiple presentations of similar or different tag or tag-group flashes can be used to update this Master Score Table to increase estimation accuracy or to have repeatable target tag selection, with the Master Score Table evaluated each time.

Conclusion

In summary, systems and methods are described herein for use in the implementation of an integrated hybrid Brain Computer Interface operable by a user in real-time. The disclosed system includes an eye-movement tracking system to implement a pointing control feature and a brain activity tracking system to implement an action control feature. Both features are implemented through the presentation of a UI/UX strategically designed to enable high speed and accurate operation, Additionally, the disclosed systems and methods are configured to be hardware agnostic to implement a real-time BCI on any suitable platform to mediate user manipulation of virtual, augmented or real environments. FIG. 11 shows an illustration of the usage space of the inventive BCI system and methods.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

The invention claimed is:

1. An apparatus, comprising:
a display configured to present a control interface to a user, the control interface including a plurality of control items each associated with an action;
a neural recording device configured to record neural signals associated with the user; and
an interfacing device operatively coupled to the display and the neural recording device, the interfacing device including:
a memory; and
a processor operatively coupled to the memory and configured to:

present, via the control interface, a stimulus including a set of control items, each control item from the set of control items presented at a predetermined location on the control interface;
receive, from the neural recording device, a set of neural signals associated with the stimulus after presenting the stimulus;
classify the set of neural signals to identify a control signal from the set of neural signals associated with the stimulus, the control signal indicative of a user's intent;
calculate a probability metric associated with each control item from the set of control items included in the stimulus, the probability metric indicating a probability that the control signal was evoked by that control item included in that stimulus from the set of control items;
determine a first score associated with each control item from the set of control items, the first score based on the probability metric associated with that control item:
determine a second score associated with each control item from the set of control items, the second score based on the predetermined location of presentation of that control item with respect to the predetermined location of presentation of at least one other control item from the remaining control items from the set of control items; and
determine a point of focus of the user based on the first score and the second score associated with each control item from the set of control items, the point of focus associated with at least one control item from the set of control items.

2. The apparatus of claim 1, wherein:
the neural signals include electroencephalogram (EEG) signals including at least one of a Event Related Potentials (ERPs), a motor imagery signal, steady state visual evoked potentials (SSVEPs), transitory visual evoked potentials (TVEPs), brain state commands, visual evoked potentials (VEPs), evoked potentials like the P300 evoked potential, sensory evoked potentials, motor evoked potentials, sensorimotor rhythms such as the mu rhythm or beta rhythm, event related desynchronization (ERDs), event-related synchronization (ERSs), slow cortical potentials (SCPs), or a brain state dependent signal,
the processor configured to classify the set of neural signals is further configured to process the set of neural signals for each stimulus from the set of stimuli to extract information associated with a set of features from the EEG signals, and
the processor is configured to determine the first score associated with each control item from the set of control items using the information associated with the set of features.

3. The apparatus of claim 2, wherein the set of features includes at least one of: an amplitude of a response included in a neural signal, a duration of the response, a shape of the response, a timing of the response relative to the presentation of a stimulus from the set of stimuli, or a frequency associated with the neural signal.

4. The apparatus of claim 1, further comprising an eye-tracking device configured to record eye-movement signals associated with the user,
the processor further configured to receive, from the eye-tracking device, a set of eye-movement signals associated with the stimulus after presenting that stimulus,
the processor configured to determine the first score associated with each control item from the set of control items based on the set of neural signals and the set of eye-movement signals associated with the stimulus.

5. The apparatus of claim 1, wherein:
each control item from the set of control items is associated with a visual representation, and
the processor is configured to change an appearance of the visual representation associated with each control item from the set of control items included in that stimulus.

6. The apparatus of claim 5, wherein changing the appearance includes a change in at least one of a size, a color, a hue, a texture, an outline, an orientation, an intensity, a thickness, or a mobility of the visual representation.

7. The apparatus of claim 1, wherein the processor is configured to determine, based on the point of focus, an action intended by the user.

8. The apparatus of claim 7, wherein the processor is further configured to implement the action intended by the user, the action being at least one of an activation or a deactivation of a control item from the plurality of control items.

9. The apparatus of claim 8, wherein the point of focus is a first point of focus during a first time period, the action is a first action, and the processor is further configured to:
determine a second point of focus of the user during a second time period after the first time period, the second point of focus associated with at least one control item from the set of control items;
determine, based on the second point of focus, a second action intended by the user, the second action being distinct from the first action; and
implement, after implementing the first action, the second action intended by the user.

10. The apparatus of claim 1, wherein the processor is further configured to classify the set of neural signals associated with the stimulus according to at least one classification scheme using a set of statistical models.

11. A non-transitory processor-readable medium storing code representing instructions to be executed by a processor, the instructions comprising code to cause the processor to:
generate a control interface configured to be manipulated, by a user, to perform a set of actions;
present, via the control interface, a stimulus to the user, the stimulus including a set of control items, each control item from the set of control items being associated with at least one action from the set of actions and presented at a predetermined location on the control interface;
receive, after presenting the stimulus to the user, information associated with the user from a neural recording device, the information including a set of neural signals associated with the stimulus;
classify the set of neural signals to identify a control signal from the set of neural signals associated with the stimulus, the control signal indicative of a user's intent;
calculate a probability metric associated with each control item from the set of control items included in the stimulus, the probability metric indicating a probability that the control signal was evoked by that control item included in that stimulus from the set of control items;

determine a first score associated with each control item from the set of control items, the first score based on the probability metric associated with that control item;

determine a second score associated with each control item from the set of control items, the second score based on the predetermined location of presentation of that control item with respect to the predetermined location of presentation of at least one other control item from the remaining control items from the set of control items; and determine a point of focus of the user based on the first score and the second score associated with each control item form the set of control items.

12. The non-transitory processor-readable medium of claim 11, wherein:

the set of neural signals including electroencephalogram (EEG) signals including at least one of Event Related Potentials (ERPs), a motor imagery signal, steady state visual evoked potentials (SSVEPs), transitory visual evoked potentials (TVEPs), brain state commands, visual evoked potentials (VEPs), evoked potentials like the P300 evoked potential, sensory evoked potentials, motor evoked potentials, sensorimotor rhythms such as the mu rhythm or beta rhythm, event related desynchronization (ERDs), event-related synchronization (ERSs), slow cortical potentials (SCPs) or a brain state dependent signal, the instructions further comprising code to cause the processor to process the neural signals to extract information associated with a set of features from the EEG signals, and the code to cause the processing to determine the first score associated with each control item from the set of control items includes code to cause the processor to determine the first score associated with each control item from the set of control items using the information associated with the set of features.

13. The non-transitory processor-readable medium of claim 11, wherein:

the code to cause the processor to determine the first score associated each control item form the set of control items includes code to cause the processor to:

determine based on the point of focus of the user, an action intended by the user.

14. The non-transitory processor-readable medium of claim 11, wherein:

the code to cause the processor to determine the point of focus of the user includes code to cause the processor to determine the point of focus of the user based at least in part on a weighted average of the first score and the second score.

15. The non-transitory processor-readable medium of claim 11, wherein:

the code to cause the processor to determine the first score associated with each control item from the set of control items includes code to cause the processor to determine the first score based on a time of presentation of the control item from the set of control items.

16. The non-transitory processor-readable medium of claim 11, the instructions further comprising code to cause the processor to:

receive eye-movement signals of the user from an eye-tracking device; and determine, based on the eye-movement signals, a set of oculomotor scores associated with each control item from the set of control items, the code to cause the processor to determine the point of focus of the user including code to cause the processor to determine the point of focus of the user further based on the set of oculomotor scores.

17. The non-transitory processor-readable medium of claim 11, wherein:

the code to cause the processor to determine the point of focus of the user includes code to cause the processor to determine the point of focus of the user based at least in part on a weighted average of the first score, the second score and the oculomotor score associated with each control item from the set of control items.

18. The non-transitory processor-readable medium of claim 11, wherein:

the code to cause the processor to classify the set of neural signals includes code to cause the processor to:

select a set of classifiers from a plurality of classifiers based on evaluating a set of performance parameters associated with the plurality of classifiers;

generate a ensemble classifier using the set of classifiers; and classify the set of neural signals using the ensemble classifier.

19. A method, comprising:

presenting a stimulus via a control interface to a user, the stimulus including a set of control items associated with a set of actions;

receiving, from a neural recording device, a set of neural signals associated with behavior of the user;

classifying the set of neural signals using a model to identify a control signal from the set of neural signals associated with the stimulus, the control signal indicative of an intent of the user;

calculating a probability metric associated with each control item from the set of control items included in the stimulus, the probability metric indicating a probability that the control signal was evoked by that control item included in that stimulus from the set of control items;

generating a first score associated with each control item from the set of control items, the first score based on the probability metric associated with that control item;

determining a second score associated with each control item from the set of control items, the second score based on the predetermined location of presentation of that control item with respect to the predetermined location of presentation of at least one other control item from the remaining control items from the set of control items;

determining a point of focus of the user based on the first score and the second score associated with each control item from the set of control items; and determining, based on the point of focus, a predicted action intended by the user.

20. The method of claim 19, further comprising:

receiving feedback information associated with an actual action intended by the user; and updating the model based on a comparison between the predicted action intended by the user and the actual action intended by the user.

* * * * *